United States Patent
Thirring et al.

(10) Patent No.: US 8,173,685 B2
(45) Date of Patent: May 8, 2012

(54) PLEUROMUTILIN DERIVATIVES AND THEIR USE AS ANTIMICROBIALS

(75) Inventors: Klaus Thirring, Vienna (AT); Werner Heilmayer, Zillingtal (AT)

(73) Assignee: Nabriva Therapeutics AG, Vienna (AT)

( * ) Notice: Subject to any disclaimer, the term of this patent is extended or adjusted under 35 U.S.C. 154(b) by 237 days.

(21) Appl. No.: 12/668,769

(22) PCT Filed: Jul. 11, 2008

(86) PCT No.: PCT/AT2008/000254
§ 371 (c)(1),
(2), (4) Date: Mar. 11, 2010

(87) PCT Pub. No.: WO2009/009812
PCT Pub. Date: Jan. 22, 2009

(65) Prior Publication Data
US 2010/0197734 A1   Aug. 5, 2010

(30) Foreign Application Priority Data
Jul. 13, 2007   (EP) ..................... 07450124

(51) Int. Cl.
*A61K 31/47* (2006.01)
*A61K 31/215* (2006.01)
*C07D 211/76* (2006.01)
*C07C 321/28* (2006.01)
*C07C 69/76* (2006.01)

(52) U.S. Cl. .......... 514/354; 514/530; 546/300; 560/17; 560/61

(58) Field of Classification Search .................. None
See application file for complete search history.

(56) References Cited

U.S. PATENT DOCUMENTS
2005/0215637 A1* 9/2005 Ascher et al. ................. 514/550

FOREIGN PATENT DOCUMENTS
| GB | 1 312 148 | 4/1973 |
| WO | 00/27790 | 5/2000 |
| WO | 01/09095 A1 | 2/2001 |
| WO | 2004/089886 A1 | 10/2004 |
| WO | 2007/000001 A2 | 1/2007 |

OTHER PUBLICATIONS

Kazuo Takimiya, et al "Synthesis, Molecular Structure, and Propoerties of 1,9-Dithia[2.2]metacyclophane" Chemistry Express, vol. 7, No. 11, pp. 865-868 (1992).
National Committee for Clinical Laboratory Standards (NCCLS) vol. 24, No. 2, M11-A5, Methods for Antimicrobal Susceptibility Testing of Anaerobic Bacteria; Approved Standard; Sixth Edition (2004).
Item 7694 Pleuromutilin, The Merck Index, 12th edition, p. 1298.

* cited by examiner

*Primary Examiner* — Paul A Zucker
(74) *Attorney, Agent, or Firm* — Workman Nydegger

(57) ABSTRACT

A compound of formula (I) or of formula (II) wherein X is oxygen or sulfur, and Y is a residue of pipecolic acid or a residue of an amino acid, preferably a naturally occurring amino acid.

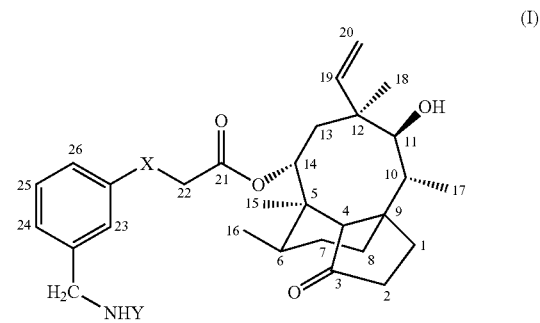

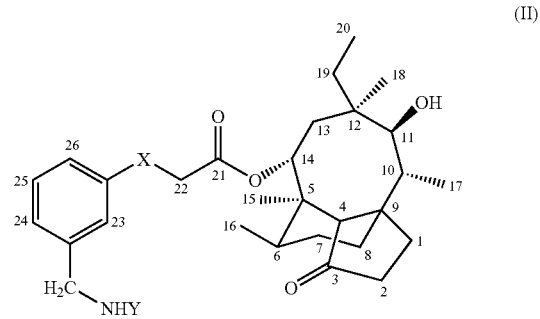

19 Claims, No Drawings

PLEUROMUTILIN DERIVATIVES AND THEIR USE AS ANTIMICROBIALS

The present invention relates to organic compounds, such as pleuromutilins.

Pleuromutilin, a compound of formula

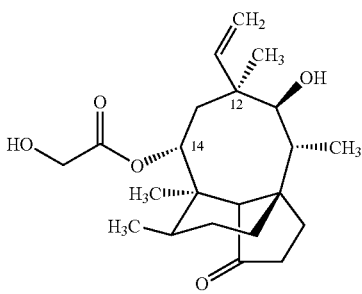

is a naturally occurring antibiotic, e.g. produced by the basidomycetes *Pleurotus mutilus* and *P. passeckerianus*, see e.g. The Merck Index, 12th edition, item 7694. A number of further pleuromutilins containing the ring structure principle of pleuromutilin and being substituted at the hydroxy group have been developed, e.g. as antimicrobials.

We have now found pleuromutilins with interesting activity.

According to one aspect of the invention there are provided compounds of formula (I)

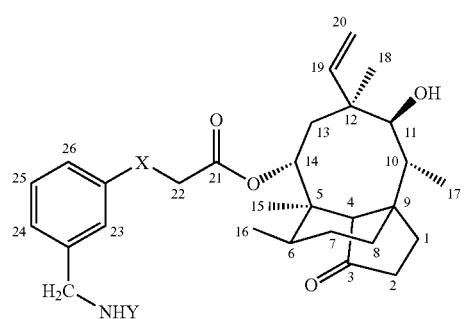

or of formula (II)

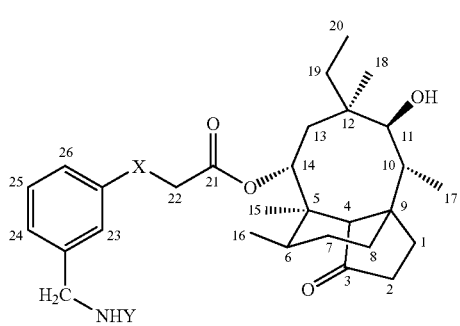

wherein
X is oxygen or sulfur, and
Y is a residue of pipecolic acid or a residue of an amino acid, preferably a naturally occurring amino acid. The amino acid may be present in D or in L form and is bound via the CO group of its carboxylic group to the nitrogen.

In another aspect of the invention there are provided compounds selected from the group consisting of 14-O-[(3-{[((R)-Piperidine-2-carbonyl)-amino]-methyl}-phenylsulfanyl)-acetyl]-mutilin, 14-O-[(3-{[((R)-2-Amino-3-methyl)-butyrylamino]-methyl}-phenylsulfanyl)-acetyl]-mutilin, 14-O-[(3-{[((2R,4R)-4-Hydroxy-pyrrolidine-2-carbonyl)-amino]-methyl}-phenylsulfanyl)-acetyl]-mutilin, 14-O-[(3-{[(S)-2-Amino-3-(3H-imidazol-4-yl)-propylamino]-methyl}-phenylsulfanyl)-acetyl]-mutilin, 14-O-[(3-{[(R)-2-Amino-propionylamino]-methyl}-phenylsulfanyl)-acetyl]-mutilin, 14-O-[(3-{[2-(2-Amino-acetylamino)-acetylamino]-methyl}-phenylsulfanyl)-acetyl]-mutilin, 14-O-[(3-{[((R)-Pyrrolidine-2-carbonyl)-amino]-methyl}-phenylsulfanyl)-acetyl]-mutilin, 14-O-[(3-{[(R)-2-Amino-3-(4-hydroxy-phenyl)-propionylamino]-methyl}-phenylsulfanyl)-acetyl]-mutilin, 14-O-[(3-{[2-Amino-acetylamino]-methyl}-phenylsulfanyl)-acetyl]-mutilin, 14-O-[(3-{[(S)-2-((S)-2-Amino-propionylamino)-propionylamino]-methyl}-phenylsulfanyl)-acetyl]-mutilin, 14-O-[(3-{[((S)-2-Amino-3-methyl)-butyrylamino]-methyl}-phenylsulfanyl)-acetyl]-mutilin, 14-O-[(3-{(2-[((R)-Pyrrolidine-2-carbonyl)-amino]-acetylamino)-methyl}-phenylsulfanyl)-acetyl]-mutilin, 14-O-[(3-{[((2R,3S)-2-Amino-3-hydroxy)-butyrylamino]-methyl}-phenylsulfanyl)-acetyl]-mutilin, 14-O-[(3-{[(R)-2,6-Diamino-hexanoylamino]-methyl}-phenylsulfanyl)-acetyl]-mutilin, 14-O-[(3-{[(R)-2-Amino-3-(1H-indol-3-yl)-propylamino]-methyl}-phenylsulfanyl)-acetyl]-mutilin, 14-O-[(3-{[(R)-2-Amino-3-phenyl-propionylamino]-methyl}-phenylsulfanyl)-acetyl]-mutilin, 14-O-[(3-{[(R)-2-Amino-3-carbamoyl-propionylamino]-methyl}-phenylsulfanyl)-acetyl]-mutilin, 14-O-[(3-{[(S)-2,6-Diamino-hexanoylamino]-methyl}-phenylsulfanyl)-acetyl]-mutilin, 14-O-[(3-{[(S)-2-((S)-2-Amino-4-methyl-pentanoylamino)-4-methyl-pentanoylamino]-methyl}-phenylsulfanyl)-acetyl]-mutilin, 14-O-[(3-{[((R)-2-Amino-3-hydroxy)-propionylamino]-methyl}-phenylsulfanyl)-acetyl]-mutilin, 14-O-[(3-{[(S)-2-Amino-propylamino]-methyl}-phenylsulfanyl)-acetyl]-mutilin, 14-O-[(3-{[(R)-2-Amino-4-carbamoyl-butyrylamino]-methyl}-phenylsulfanyl)-acetyl]-mutilin, 14-O-[(3-{[(S)-1-(2-Amino-acetyl)-pyrrolidine-2-carbonyl)-amino]-methyl}-phenylsulfanyl)-acetyl]-mutilin, 14-O-[(3-{[(R)-2-Amino-3-(3H-imidazol-4-yl)-propionylamino]-methyl}-phenylsulfanyl)-acetyl]-mutilin, 14-O-[(3-{[((2S,4R)-4-Hydroxy-pyrrolidine-2-carbonyl)-amino]-methyl}-phenylsulfanyl)-acetyl]-mutilin, 14-O-[(3-{[(S)-Piperidine-2-carbonyl)-amino]-methyl}-phenylsulfanyl)-acetyl]-mutilin, 14-O-[(3-{[((S)-Pyrrolidine-2-carbonyl)-amino]-methyl}-phenylsulfanyl)-acetyl]-mutilin, 14-O-[(3-{[(S)-2-Amino-3-(4-hydroxy-phenyl)-propionylamino]-methyl}-phenylsulfanyl)-acetyl]-mutilin, 14-O-[(3-{[(S)-2-Amino-3-phenyl-propionylamino]-methyl}-phenylsulfanyl)-acetyl]-mutilin, 14-O-[(3-{[(S)-2-Amino-3-hydroxy)-propionylamino]-methyl}-phenylsulfanyl)-acetyl]-mutilin, 14-O-[(3-{[((2S,3R)-2-Amino-3-hydroxy)-butyrylamino]-methyl}-phenylsulfanyl)-acetyl]-mutilin, 14-O-[(3-{[((R)-2-Amino-3-hydroxy)-propionylamino]-methyl}-phenoxy)-acetyl]-mutilin,
14-O-[(3-{[((R)-Pyrrolidine-2-carbonyl)-amino]-methyl}-phenoxy)-acetyl]-mutilin,
14-O-[(3-{[(S)-2-Amino-3-(4-hydroxy-phenyl)-propionylamino]-methyl}-phenoxy)-acetyl]-mutilin,
14-O-[(3-{[(R)-2-Amino-3-(4-hydroxy-phenyl)-propionylamino]-methyl}-phenoxy)-acetyl]-mutilin,
14-O-[(3-{[((R)-Pyrrolidine-2-carbonyl)-amino]-methyl}-phenoxy)-acetyl]-19,20-dihydromutilin,
14-O-[(3-{[((R)-2-Amino-3-hydroxy)-propionylamino]-methyl}-phenoxy)-acetyl]-19,20-dihydromutilin,
14-O-[(3-{[(S)-2-Amino-3-(4-hydroxy-phenyl)-propionylamino]-methyl}-phenoxy)-acetyl]-19,20-dihydromutilin.

It turned out that the antimicrobial activity against clinical relevant bacterial pathogens (*Staphylococcus aureus, Enterococcus faecalis, Streptococcus pneumoniae, Moraxella catarrhalis* and *Escherichia coli*, see Table 1 hereinafter) of said pleuromutilin-derivatives is particularly enhanced when the phenyl-ring carries a saturated carbon atom bearing a residue of pipecolic acid or a residue of an amino acid, preferably a naturally occurring amino acid in meta position (in relation to the oxygen/sulfur bound to the phenyl-ring).

A compound provided by the present invention is herein also designated as "compound(s) of (according to) the present invention". A compound of the present invention includes mutilin-14-yl acetic acid esters, e.g. as explicitly defined above, and a compound of formulas I and II. A compound of the present invention includes a compound in any form, e.g. in free form, in the form of a salt, in the form of a solvate and in the form of a salt and a solvate.

The compounds of the present invention may be in crystalline or non-crystalline form, and, if crystalline, may optionally be hydrated or a solvate. When some of the compounds of this invention are allowed to crystallise or are recrystallised from organic solvents, solvent of crystallisation may be present in the crystalline product.

This invention includes within its scope such solvates. Similarly, some of the compounds of this invention may be crystallised or recrystallised from solvents containing water. In such cases water of hydration may be present in the crystalline product. This invention includes within its scope stoichiometric hydrates as well as compounds containing variable amounts of water that may be produced by processes such as lyophilisation.

In another aspect the present invention provides a compound of the present invention in the form of a salt.

Such salts include preferably pharmaceutically acceptable salts, although pharmaceutically unacceptable salts are included, e.g. for preparation/isolation/purification purposes.

A salt of a compound of the present invention includes a metal salt or an acid addition salt.

Metal salts include for example alkali or earth alkali salts; acid addition salts include salts of a compound of the present invention with an acid, e.g. hydrogen fumaric acid, fumaric acid, naphthaline-1,5-sulphonic acid, hydrochloric acid, deuterochloric acid; preferably hydrochloric acid.

A compound of the present invention in free form may be converted into a corresponding compound in the form of a salt; and vice versa. A compound of the present invention in free form or in the form of a salt and in the form of a solvate may be converted into a corresponding compound in free form or in the form of a salt in non-solvated form; and vice versa.

A compound of the present invention, if substituted accordingly, may exist in the form of isomers and mixtures thereof; e.g. optical isomers, diastereoisomers, cis/trans conformers. A compound of the present invention may e.g. contain asymmetric carbon atoms and may thus exist in the form of enantiomers or diastereoisomers and mixtures thereof, e.g. racemates. Substituents at any asymmetric carbon atom may be present in the (R)—, (S)- or (R,S)-configuration, preferably in the (R)- or (S)-configuration.

Isomeric mixtures may be separated as appropriate, e.g. according, e.g. analogously, to a method as conventional, to obtain pure isomers. The present invention includes a compound of the present invention in any isomeric form and in any isomeric mixture.

The present invention also includes tautomers of a compound of the present invention, where tautomers can exist.

Any compound as described herein, e.g. a compound of the present invention and intermediates in their production may be prepared as appropriate, e.g. according, e.g. analogously, to a method as conventional, e.g. or as specified herein.

A compound as described herein, e.g. a compound of the present invention and intermediates in their production may be converted into a corresponding salt, according, e.g. analogously, to a method as conventional, e.g. by treatment with an acid, or, metal base, respectively, to obtain an acid addition salt, or, a metal salt, respectively and vice versa, a compound obtained by a process provided by the present invention in the form of a salt, may be converted into the corresponding compound in the form of a free base, according, e.g. analogously, to a method as conventional, e.g. by treatment with an acid if a metal salt is obtained and by treating with a metal base, e.g. a metal hydroxide if an acid addition salt is obtained.

For example, the compounds of the present invention show antimicrobial, e.g. antibacterial, activity against gram positive bacteria, such as coagulase-positive and coagulase-negative Staphylococci, e.g. *Staphylococcus aureus, Styphylococcus epidermis, Staphylococcus haemolyticus, Streptococci*, e.g. *Streptococcus pyogenes, Streptococcus pneumoniae, Streptococcus agalacticae, Enterococci*, e.g. *Enterococcus faecium* and Moraxellaceae, e.g. *Moraxella catarrhalis, Pasteurellaceae*, e.g. *Haemophilus influenzae*, as well as against Mycoplasmactaceae, Chlamydiaceae, e.g. *Chlamydia trachomatis, Chlamydia pneumoniae* and obligatory anaerobes, e.g. *Bacteroides fragilis, Clostridium difficile*; in vitro in the Agar Dilution Test or Microdilution Test according to the Clinical and Laboratory Standards Institute (CLSI, former National Committee for Clinical Laboratory Standards (NC-CLS) 2006, Document M7-A7 Vol. 26, No. 2: "Methods for dilution Antimicrobial Susceptibility Tests for Bacteria that Grow Aerobically—Seventh Edition, Approved Standard"; and in the in vitro determination of the antibacterial activity against anaerobic bacteria according to National Committee for Clinical Laboratory Standards (NCCLS) VOL. 24, No. 2, M11-A5, Methods for Antimicrobal Susceptibility Testing of Anaerobic Bacteria; Approved Standard; Sixth Edition (2004) and in vivo in the septicaemic mouse model against *Staphylococcus aureus*.

Compounds of the present invention are therefore suitable for the treatment and prevention of diseases which are mediated by microbes, e.g. by bacteria. Diseases which also may be treated include e.g. diseases mediated by *Helicobacter*, such as *Helicobacter pylori*, and diseases mediated by *Mycobacterium tuberculosis*, diseases mediated by *Legionella pneumophila* or Neisseriaceae, diseases which also may be treated include in general inflammatory diseases, where microbes are mediating said inflammation, e.g. including acne.

Compounds of the present invention are preferably useful to treat skin and soft tissue infections, for example epidermal infections like impetigo, bullous impetigo or eethyma, dermal infections like erysipelas, cellulites, erythrasma or necrotizing fasciitis, follicular infections like folliculitis, furunculosis or carbunculosis, other infections like paronychia, dactylitis, botryomycosis, mastitis, secondarily infected skin lesions, secondarily infected dermatoses, for the decolonization of bacterial carriers, e.g. decolonisation of nasal *Staphylococcus aureus* carriers, and acne, by topical application.

Accordingly, in a further aspect the present invention provides the use of a compound of the present invention or a pharmaceutically acceptable salt or derivative or solvate thereof, in the preparation of a medicament adapted for topical administration for use in the treatment of skin and soft tissue infections and also in the treatment of acne in humans. The present invention also provides the use of a compound of the present invention, or a pharmaceutical acceptable derivative thereof, in the manufacture of a medicament for use in the treatment of a skin or soft tissue infection.

In another aspect the present invention provides a compound of the present invention for use as a pharmaceutical, preferably as an antimicrobial, such as an antibiotic, e.g. and an anti-anaerobic.

In a further aspect the present invention provides a compound of the present invention for use in the preparation of a medicament for the treatment of diseases, mediated by microbes, such as bacterials, for example
- diseases mediated by bacteria, e.g. selected from Staphylococci, Streptococci, Enterococci;
- diseases mediated by *Helicobacter*
- diseases mediated by *Legionella, Neisseriaceae, Moraxellaceae, Pasteurellaceae, Corynebacteria,*
- diseases mediated by *Mycobacterium tuberculosis,*
- e.g. diseases mediated by Mycoplasmataceae, Chlamydiaceae and obligatory anaerobes,
- for the treatment of acne, and/or
- for the decolonization of individuals colonized with bacteria.

In a further aspect the present invention provides a method of treatment of diseases mediated by microbes which comprises administering to a subject in need of such treatment an effective amount of a compound of the present invention e.g. in the form of a pharmaceutical composition.

In a further aspect the present invention provides a method of treatment of acne which comprises administering to a subject in need of such treatment an effective amount of a compound of the present invention e.g. in the form of a pharmaceutical composition.

Treatment includes treatment and prophylaxis.

For antimicrobial and acne treatment, the appropriate dosage will, of course, vary depending upon, for example, the chemical nature and the pharmakokinetic data of a compound of the present invention employed, the individual host, the mode of administration and the nature and severity of the conditions being treated. However, in general, for satisfactory results in larger mammals, for example humans, an indicated daily dosage is in the range from about 0.01 to 3 g of a compound of the present invention conveniently administered, for example, in divided doses up to four times a day.

A compound of the present invention may be administered by any conventional route, for example enterally, e.g. including nasal, buccal, rectal, oral, administration; parenterally, e.g. including intravenous, intramuscular, subcutaneous administration; or topically, e.g. including epicutaneous, intranasal, intratracheal administration, e.g. in form of coated or uncoated tablets, capsules, injectable solutions or suspensions, e.g. in the form of ampoules, vials, in the form of semi-solid formulations, e.g. ointments, creams, gels, pastes, in the form of inhaler powder, foams, tinctures, lip sticks, concealer sticks, drops, sprays, or in the form of suppositories, e.g. in analogous manner to macrolides, such as erythromycins, e.g. clarithromycin or azithromycin.

A compound of the present invention may be administered in the form of a pharmaceutically acceptable salt, e.g. an acid addition salt or metal salt; or in free form; optionally in the form of a solvate. A compound of the present invention in the form of a salt exhibit the same order of activity as the compound in free form; optionally in the form of a solvate.

A compound of the present invention may be used for pharmaceutical treatment according to the present invention alone or in combination with one or more other pharmaceutically active agents. Such other pharmaceutically active agents include e.g. other antibiotics and antiinflammatory agents, and, if a compound of the present invention is used in the treatment of acne, other pharmaceutically agents include furthermore agents which are active against acne or used for the decolonization/sterilisation of bacterial carriers. Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect the present invention provides a pharmaceutical composition comprising a compound of the present invention, e.g. including a compound of formula I, in free form or in the form of a pharmaceutically acceptable salt; e.g. and/or in the form of a solvate; in association with at least one pharmaceutical, excipient, e.g. carrier or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers.

In another aspect the present invention provides a pharmaceutical composition according to the present invention, further comprising another pharmaceutically active agent.

Such pharmaceutical compositions may be manufactured according, e.g. analogously, to a method as conventional, e.g. by mixing, granulating, coating, dissolving or lyophilizing processes.

Unit dosage form may contain, for example, from about 0.01 mg to about 3000 mg, such as 1 mg to about 1000 mg.

The compounds of the present invention are additionally suitable as veterinary agents, e.g. veterinary active compounds, e.g. in the prophylaxis and in the treatment of microbial, e.g. bacterial diseases, in animals, such as fowl, pigs and calves; e.g. and for diluting fluids for artificial insemination and for egg-dipping techniques.

In another aspect the present invention provides a compound of the present invention for use as a veterinary agent.

In a further aspect the present invention provides a compound of the present invention for the preparation of a veterinary composition which is useful as a veterinary agent.

In another aspect the present invention provides a veterinary method for the prophylaxis and in the treatment of microbial, e.g. bacterial diseases which comprises administering to a subject in need of such treatment an effective amount of a compound of the present invention, e.g. in the form of a veterinary composition.

For use of the active compounds of the present invention as a veterinary agent, the dosage will of course vary depending upon the size and age of the animal and the effect desired; for example for prophylactic treatment relatively low doses would be administered over a longer time period, e.g. 1 to 4 weeks. Preferred doses in drinking water are from 0.0125 to 0.05 weight by volume, particularly 0.0125 to 0.025; and in foodstuffs from 20 to 400 g/metric ton, preferably 20 to 200 g/metric ton. It is preferred to administer the active compounds of the present invention as a veterinary agent to hens in drinking water, to pigs in foodstuff and to calves orally or parenterally, e.g. in the form of oral or parenteral preparations.

The invention is further described by reference to the following examples. These examples are provided for illustration purposes only and are not intended to be limiting the present invention in any way.

The Following Abbreviations are Used
BOC tert-Butoxy-carbonyl
DCC N,N'-Dicyclohexylcarbodiimide
DMAP 4-Dimethylaminopyridine
DMF N,N-Dimethylformamide
EtOAc Ethyl acetate
h hour(s)
MeOH Methanol
rt room temperature
THF Tetrahydrofurane

EXAMPLES

Example 1

14-O-[(3-{[((R)-Piperidine-2-carbonyl)-amino]-methyl}-phenylsulfanyl)-acetyl]-mutilin Step 1: Pleuromutilintosylate To a solution of 18.63 g (49.2 mmol) of Pleuromutilin and 9.39 g (49.2 mmol) of toluenesulfonylchloride in 1400 mL of methylethylketone a solution of 4.98 g (49.2 mmol) of triethylamine in 300 mL of methylethylketone is slowly added at ambient temperature. The reaction is stirred for 24 h at ambient temperature, the formed precipitate is filtered off and 2800 mL of water is added to the solution. The solution is extracted three times with ethyl acetate, the organic phase is dried with $Na_2SO_4$ and evaporated to dryness under reduced pressure. The crude product is used for the next step without further purification.

$^1$H-NMR (400 MHz, DMSO-$d_6$, δ, ppm, characteristic signals): 0.49 (d, 3H, J=7 Hz, $CH_3$-16); 0.8 (d, 3H, J=7 Hz, $CH_3$-17); 1.02 (s, 3H, $CH_3$-18); 1.29 (s, 3H, $CH_3$-15); 2.38 (bs, 1H, H-4); AB-system ($u_A$=4.75, $u_B$=4.62, J=16 Hz, $CH_2$-22); 5.00 (m, 2H, H-20); 5.52 (d, 1H, J=8 Hz, H-14); 6.04 (dd, 1H, J=11 and 18 Hz, H-19); 7.46 (d, 2H, J=8 Hz, H-24); 7.79 (d, 2H, J=8 Hz, H-23).

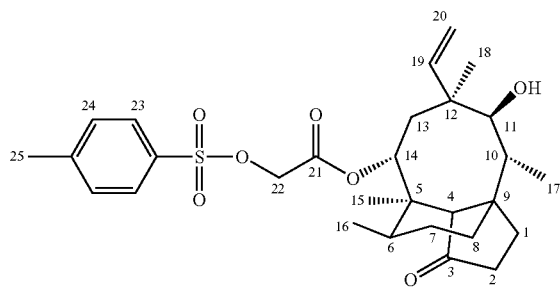

Step 2: 14-O-[(3-Hydroxymethyl-phenylsulfanyl)-acetyl]-mutilin

To 1.96 g (14 mmol) of (3-Mercapto-phenyl)-methanol [prepared from 3-Mercaptobenzoic acid according to: Chemistry Express, Vol 7, No. 11, pp. 865-868 (1992)] in 90 mL of absolute ethanol 322 mg (14 mmol) of sodium is added. After stirring the reaction for 30 min at ambient temperature a solution of 7.45 g (14 mmol) of Pleuromutilintosylate in 130 mL of methylethylketone is added and the reaction stirred at ambient temperature for 16 h. The reaction mixture is evaporated to dryness under reduced pressure, dissolved in ethyl acetate and extracted three times with water. The organic phase is dried with $Na_2SO_4$, evaporated to dryness under reduced pressure and the residue is chromatographed on silica gel using dichloromethane/methanol 100:1.5 as mobile phase.

The obtained material was crystalline (Fp. 139-141° C.).

$^1$H-NMR (500 MHz, $CDCl_3$, δ, ppm, characteristic signals): 0.68 (d, 3H, J=7 Hz, $CH_3$-16); 0.88 (d, 3H, J=7 Hz, $CH_3$-17); 1.12 (s, 3H, $CH_3$-18); 1.42 (s, 3H, $CH_3$-15); 2.06 (bs, 1H, H-4); 3.32 (t, 1H, J=6 Hz, H-11); 3.59 (s, 2H, $CH_2$-22); 4.66 (s, 2H, $CH_2$-27); 5.15 and 5.30 (2×m, 2H, H-20); 5.72 (d, 1H, J=8 Hz, H-14); 6.41 (dd, 1H, J=11 and 17 Hz, H-19); 7.19 and 7.28 (2×m, 3H, H-24,25 and 26); 7.38 (s, 1H, H-23).

$^1$H-NMR (400 MHz, DMSO-$d_6$, δ, ppm, characteristic signals): 0.56 (d, 3H, J=7 Hz, $CH_3$-16); 0.79 (d, 3H, J=7 Hz, $CH_3$-17); 0.98 (s, 3H, $CH_3$-18); 1.30 (s, 3H, $CH_3$-15); 2.35 (bs, 1H, H-4); 3.37 (t, 1H, J=6 Hz, H-11); AB-system ($u_A$=3.81, $u_B$=3.74, J=16 Hz, $CH_2$-22); 4.44 (d, 2H, J=6 Hz, $CH_2$-27); 4.95 (m, 2I-1, H-20); 5.49 (d, 1H, J=8 Hz, H-14); 6.04 (m, 1H, H-19), 7.10-7.27 (4×m, 4H, H-23,24,25 and 26).

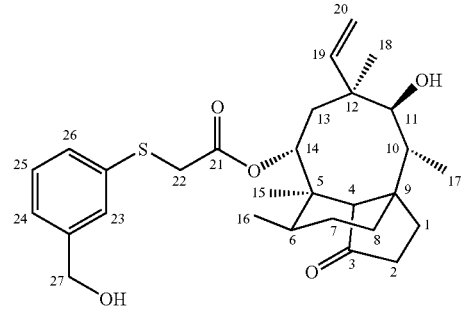

Step 3: 14-O-[(3-Methanesulfonyloxymethyl-phenylsulfanyl)-acetyl]-mutilin

To 6 g (12 mmol) of 14-O-[(3-Hydroxymethyl-phenylsulfanyl)-acetyl]-mutilin in 250 mL of dry THF 2.17 mL (20 mmol) of N-methylmorpholine and 3.06 g (18 mmol) of methanesulfonic anhydride are added together with a catalytic amount of 4-dimethylaminopyridine. The reaction mixture is allowed to stand for 2 h at ambient temperature. After addition of water the mixture is extracted with ethyl acetate and then the organic phase washed several times with water and brine. The organic phase is dried with anhydrous sodium sulfate and concentrated under reduced pressure. The organic phase is dried with anhydrous sodium sulfate, concentrated under reduced pressure and chromatographed on silica gel using dichloromethane/methanol 100:1 as mobile phase.

$^1$H-NMR (400 MHz, $CDCl_3$, δ, ppm, characteristic signals): 0.68 (d, 3H, J=7 Hz, $CH_3$-16); 0.87 (d, 3H, J=7 Hz, $CH_3$-17); 1.12 (s, 3H, $CH_3$-18); 1.40 (s, 3H, $CH_3$-15); 2.08 (bs, 1H, H-4); 2.96 (s, 3H, $CH_3$-28); 3.34 (d, 1H, J=6 Hz, H-11); 3.59 (s, 2H, $CH_2$-22); 5.15 and 5.30 (2×m, 2H, H-20);

5.72 (d, 1H, J=8 Hz, H-14); 6.40 (dd, 1H, J=11 and 17 Hz, H-19); 7.23-7.43 (m, 4H, H-23,24,25 and 26).

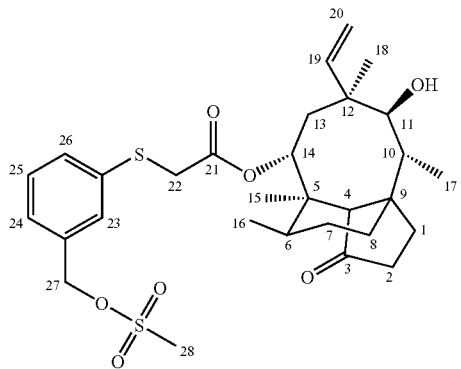

Step 4: 14-O-[(3-Azidomethyl-phenylsulfanyl)-acetyl]-mutilin

To 1 g (1.73 mmol) of 14-O-[(3-Methanesulfonyloxymethyl-phenylsulfanyl)-acetyl]-mutilin in 10 mL of DMF 449 mg (6.9 mmol) of NaN$_3$ is added. The resulting suspension is stirred for 4.5 h at 50° C. and left overnight at ambient temperature. Water and ethyl acetate are added and the organic phase washed several times with water and brine. After concentrating under reduced pressure, the residue is chromatographed on silica using CH$_2$Cl$_2$/MeOH 100:1 as mobile phase.

$^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 1.00 (s, 3H, CH$_3$-18); 1.30 (s, 3H, CH$_3$-15); 2.34 (bs, 1H, H-4); 3.37 (t, 1H, J=6 Hz, H-11); AB-system (u$_A$=3.85, u$_B$=3.78, J=16 Hz, CH$_2$-22); 4.39 (s, 2H, CH$_2$-27); 4.95 (m, 2H, H-20); 5.49 (d, 1H, J=8 Hz, H-14); 6.04 (dd, 1H, J=11 and 18 Hz, H-19); 7.18 (m, 1H, H-25); 7.32 (m, 2H, H-24 and 26); 7.34 (bs, 1H, H-23).

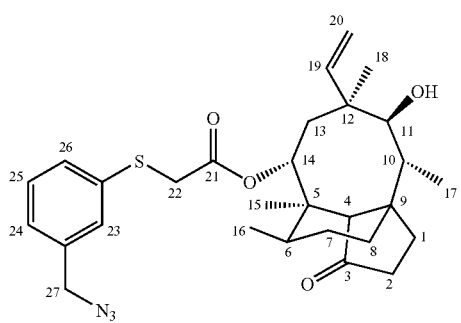

Step 5: 14-O-[(3-Aminomethyl-phenylsulfanyl)-acetyl]-mutilin hydrochloride 1 g (1.9 mmol) of 14-O-[(3-Azidomethyl)-phenylsulfanyl-acetyl]mutilin is dissolved in 30 mL of THF, 900 mg of Lindlar-catalyst is added and the reaction mixture hydrogenated for 6 h. The reaction mixture is filtered through celite, concentrated under reduced pressure and the residue is chromatographed on silica using CH$_2$Cl$_2$/MeOH 10:1 as mobile phase. The hydrochloride was obtained by dissolving 125 mg of 14-O-[(3-Aminomethyl)-phenylsulfanyl-acetyl]-mutilin in 3 mL of CH$_2$Cl$_2$ and adding 2 mL of HCl-saturated Et$_2$O. After 45 minutes the reaction was evaporated to dryness under reduced pressure.

$^1$H-NMR (400 MHz, DMSO-d$_6$, δ, ppm, characteristic signals): 0.57 (d, 3H, J=7 Hz, CH$_3$-16); 0.79 (d, 3H, J=7 Hz, CH$_3$-17); 1.00 (s, 3H, CH$_3$-18); 1.31 (s, 3H, CH$_3$-15); 2.38 (bs, 1H, H-4); 3.38 (t, 1H, J=6 Hz, H-11); AB-system (u$_A$=3.89, u$_B$=3.82, J=16 Hz, CH$_2$-22); 3.95 (s, 2H, CH$_2$-27); 4.98 (m, 2H, H-20); 5.51 (d, 1H, J=8 Hz, H-14); 6.05 (dd, 1H, J=11 and 18 Hz, H-19); 7.30 (m, 3H, H-24,25 and 26); 7.48 (s, 1H, H-23).

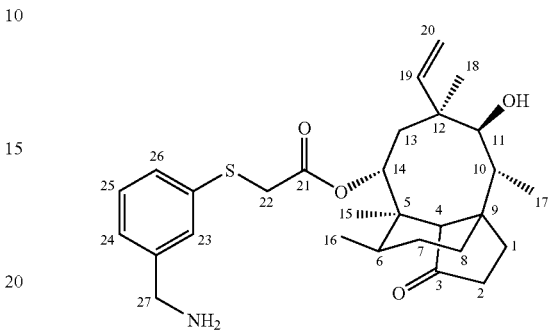

Step 6: 14-O-[(3-{[((R)-tert-Butoxycarbonylpiperidine-2-carbonyl)-amino]-methyl}-phenylsulfanyl)-acetyl]-mutilin To 200 mg (0.4 mmol) of 14-O-[(3-Aminomethyl)-phenylsulfanyl-acetyl]-mutilin in 2.5 mL of THF is added 180 mg (0.6 mmol) of BOC-D-Homoproline together with 124 mg (0.6 mmol) of DCC and 49 mg (0.4 mmol) of DMAP. The reaction is stirred for 3 h ar ambient temperature, the formed precipitate is filtered off and the filtrate is evaporated to dryness under reduced pressure. The residue is chromatographed on silica using dichloromethane/methanol 100:2 as mobile phase.

$^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 1.34 (bs, 9H, CH$_3$-33); 2.36 (bs, 1H, H-4); 3.03 and 4.56 (2×bm, 2H, CH$_2$-32); 3.38 (t, 1H, J=6 Hz, H-11); AB-system (u$_A$=3.81, u$_B$=3.74, J=16 Hz, CH$_2$-22); 3.81 (bm, 1H, H-28); 4.23 (bm, 2H, CH$_2$-27); 4.98 (m, 2H, H-20); 5.50 (d, 1H, J=8 Hz, H-14); 6.04 (m, 1H, H-19); 7.05 (d, 1H, J=7 Hz, H-23); 7.20 (m, 3H, H-24,25 and 26).

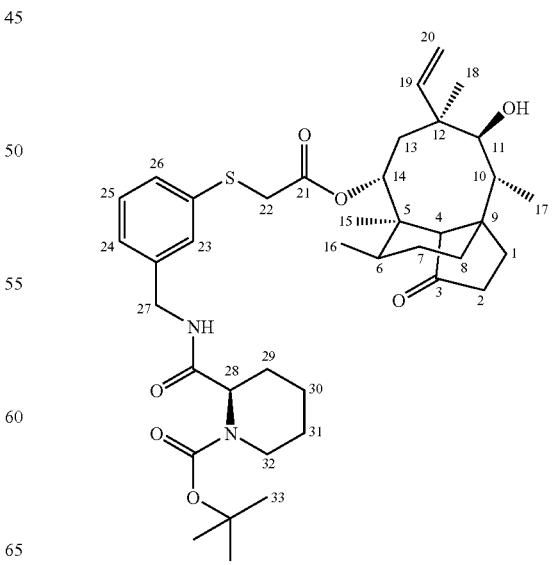

Step 7: 14-O-[(3-{[((R)-Piperidine-2-carbonyl)-amino]-methyl}-phenylsulfanyl)-acetyl]-mutilin hydrochloride 208 mg of 14-O-[(3-{[((R)-BOC-Piperidine-2-carbonyl)-amino]-methyl}-phenylsulfanyl)-acetyl]-mutilin is dissolved in 3 mL of dichloromethane and 4 mL of HCl-saturated Et$_2$O was added. The reaction was left at ambient temperature for 4 h and evaporated to dryness under reduced pressure.

$^1$H-NMR (400 MHz, DMSO-d$_6$, δ, ppm, characteristic signals): 0.58 (d, 3H, J=7 Hz, CH$_3$-16); 0.79 (d, 3H, J=7 Hz, CH$_3$-17); 0.99 (s, 3H, CH$_3$-18), 1.31 (s, 3H, CH$_3$-15); 2.36 (bs, 1H, H-4); 2.90 and 3.21 (2×m, 2H, CH$_2$-32); 3.38 (t, 1H, J=6 Hz, H-11); AB-system (u$_A$=3.84, u$_B$=3.77, J=16 Hz, CH$_2$-22); 3.78 (bm, 1H, H-28); 4.29 (d, 2H, J=6 Hz, CH$_2$-27); 4.96 (m, 2H, H-20); 5.50 (d, 1H, J=8 Hz, H-14); 6.04 (dd, 1H, J=11 and 18 Hz, H-19); 7.07 (m, 1H, H-23); 7.22 (m, 3H, H-24,25 and 26).

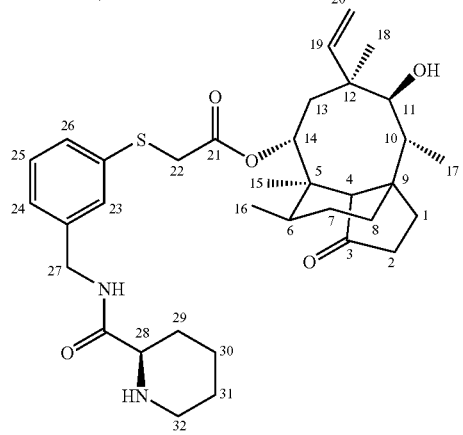

The following compounds are prepared in a similar fashion:

Example 2

14-O-[(3-{[((R)-2-Amino-3-methyl)-butyrylamino]-methyl}-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.91 and 0.92 (2×d, 6H, J=7 Hz, CH$_3$-30); 0.99 (s, 3H, CH$_3$-18); 1.31 (s, 3H, CH$_3$-15); 2.36 (bs, 1H, H-4); 3.38 (t, 1H, J=6 Hz, H-11); 3.58 (bs, 1H, H-28); AB-system (u$_A$=3.84, u$_B$=3.77, J=16 Hz, CH$_2$-22); ABX-system (u$_A$=4.34, u$_B$=4.27, J$_{AB}$=15 Hz, J$_{AX}$=6 Hz, J$_{BX}$=6 Hz, CH$_2$-27); 4.95 (m, 2H, H-20); 5.51 (d, 1H, J=8 Hz, H-14); 6.04 (dd, 1H, J=11 and 18 Hz, H-19); 7.10 (d, 1H, J=7 Hz, H-23); 7.24 (m, 3H, H-24,25 and 26).

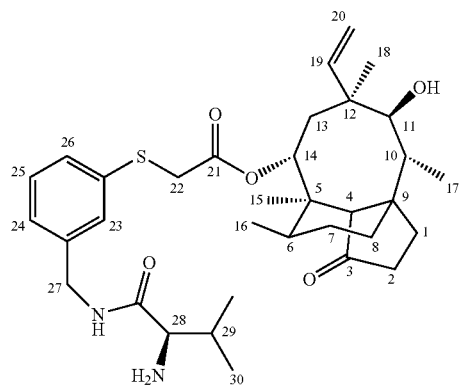

Example 3

14-O-[(3-{[((2R,4R)-4-Hydroxy-pyrrolidine-2-carbonyl)-amino]-methyl}-phenylsulfanyl)-acetyl]-mutilin hydrochloride $^1$H-NMR (400 MHz, DMSO-d$_6$, δ, ppm, characteristic signals): 0.57 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); ABX-system (u$_A$=3.20, u$_B$=3.12, J$_{AB}$=12 Hz, J$_{AX}$=5 Hz, J$_{BX}$=2 Hz, CH$_2$-31); 3.38 (t, 1H, J=6 Hz, H-11); AB-system (u$_A$=3.85, u$_B$=3.77, J=16 Hz, CH$_2$-22); 4.20-4.38 (3×m, 4H, CH$_2$-27, H-28 and 30); 4.96 (m, 2H, H-20); 5.50 (d, 1H, J=8 Hz, H-14); 6.04 (dd, 1H, J=11 and 18 Hz, H-19); 7.08 (m, 1H, H-23); 7.22 (m, 3H, H-24,25 and 26).

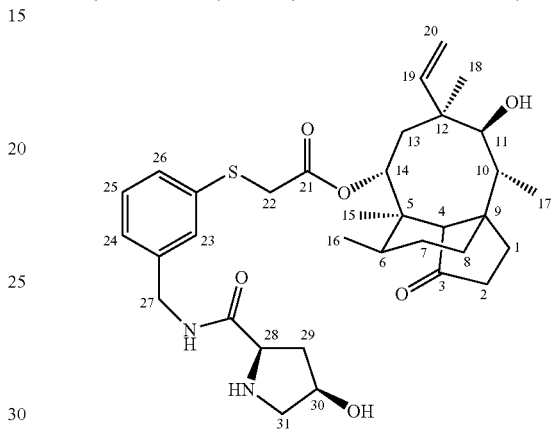

Example 4

14-O-[(3-{[(S)-2-Amino-3-(3H-imidazol-4-yl)-propionylamino]-methyl}-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); ABX-system (u$_A$=3.28, u$_B$=3.18, J$_{AB}$=16 Hz, J$_{AX}$=7 Hz, J$_{BX}$=7 Hz, CH$_2$-29); 3.37 (t, 1H, J=6 Hz, H-11); AB-system (u$_A$=3.85, u$_B$=3.78, J=16 Hz, CH$_2$-22); 4.25 (m, 3H, CH$_2$-27 and H-28); 4.95 (m, 2H, H-20); 5.50 (d, 1H, J=8 Hz, H-14); 6.04 (dd, 1H, J=11 and 18 Hz, H-19); 6.98 (m, 1H, H-23); 7.21 (m, 3H, H-24,25 and 26); 7.45 (s, 1H, H-30); 9.02 (s, 1H, H-31).

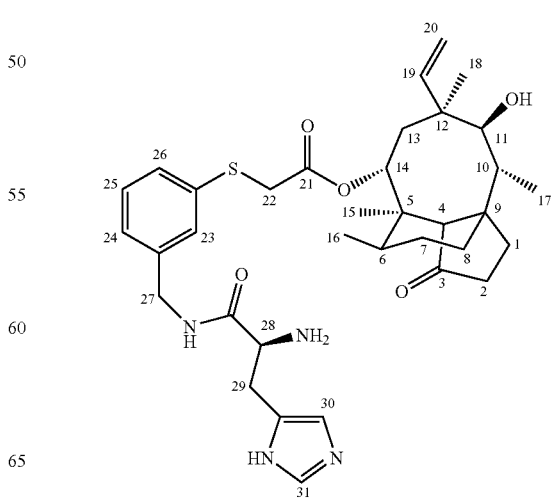

Example 5

14-O-[(3-{[(R)-2-Amino-propionylamino]-methyl}-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 1.37 (d, 3H, J=7 Hz, CH$_3$-29); 2.36 (bs, 1H, H-4); 3.38 (t, 1H, J=6 Hz, H-11); AB-system (u$_A$=3.84, u$_B$=3.77, J=16 Hz, CH$_2$-22); 3.84 (bm, 1H, H-28); 4.28 (d, 2H, J=6 Hz, CH$_2$-27); 4.95 (m, 2H, H-20); 5.50 (d, 1H, J=8 Hz, H-14); 6.04 (dd, 1H, J=11 and 18 Hz, H-19); 7.07 (d, 1H, J=7 Hz, H-23); 7.21 (m, 3H, H-24,25 and 26).

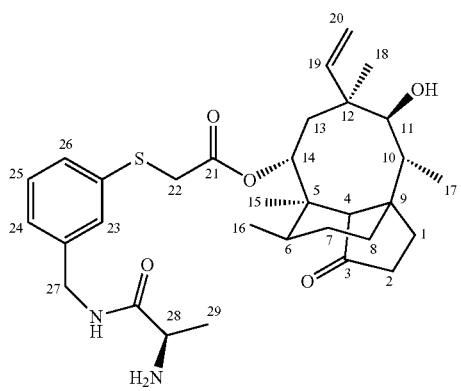

Example 6

14-O-[(3-{[2-(2-Amino-acetylamino)-acetylamino]-methyl}-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); 3.37 (t, 1H, J=6 Hz, H-11); 3.58 (m, 2H, CH$_2$-29); AB-system (u$_A$=3.84, u$_B$=3.77, J=16 Hz, CH$_2$-22); 3.84 (m, 2H, CH$_2$-28); 4.23 (d, 2H, J=6 Hz, CH$_2$-27); 4.95 (m, 2H, H-20); 5.50 (d, 1H, J=8 Hz, H-14); 6.03 (m, 1H, H-19); 7.07 (d, 1H, J=7 Hz, H-23); 7.20 (m, 3H, H-24, 25 and 26).

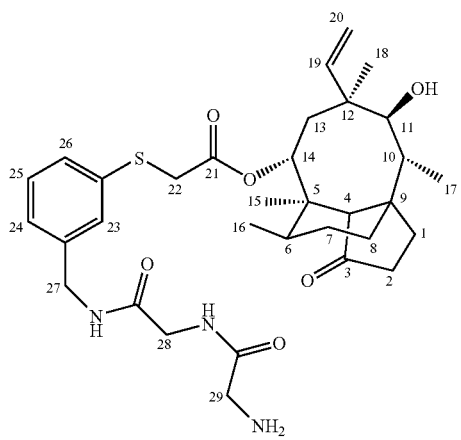

Example 7

14-O-[(3-{[((R)-Pyrrolidine-2-carbonyl)-amino]-methyl}-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); 3.19 (bm, 2H, CH$_2$-31); 3.37 (t, 1H, J=6 Hz, H-11); AB-system (u$_A$=3.84, u$_B$=3.77, J=16 Hz, CH$_2$-22); 4.19 (bm, 1H, H-28); 4.30 (m, 2H, CH$_2$-27); 4.95 (m, 2H, H-20); 5.50 (d, 1H, J=8 Hz, H-14); 6.04 (m, 1H, H-19); 7.08 (m, 1H, H-23); 7.23 (m, 3H, H-24,25 and 26).

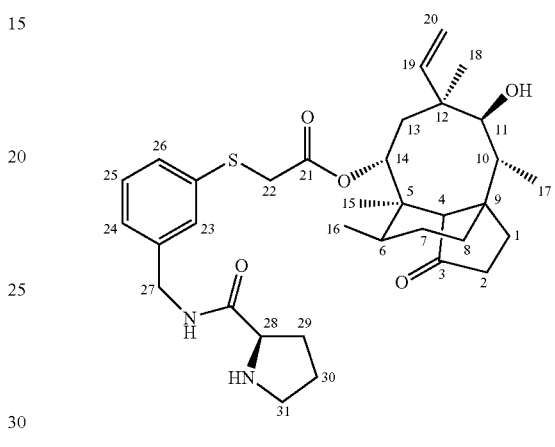

Example 8

14-O-[(3-{[(R)-2-Amino-3-(4-hydroxy-phenyl)-propionylamino]-methyl}-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); ABX-system (u$_A$=2.94, u$_B$=2.88, J$_{AB}$=15 Hz, J$_{AX}$=7 Hz, J$_{BX}$=7 Hz, CH$_2$-29); 3.37 (t, 1H, J=6 Hz, CH$_2$-22); AB-system (u$_A$=3.84, u$_B$=3.77, J=16 Hz, CH$_2$-22); 3.92 (t, 1H, J=7 Hz, H-28); ABX-system (u$_A$=4.27, u$_B$=4.20, J$_{AB}$=15 Hz, J$_{AX}$=6 Hz, J$_{BX}$=6 Hz, CH$_2$-27); 4.95 (m, 2H, H-20); 5.50 (d, 1H, J=8 Hz, H-14); 6.04 (dd, 1H, J=11 and 18 Hz, H-19); 6.68 (d, 2H, J=8 Hz, H-31); 6.86 (m, 1H, H-23); 6.99 (d, 2H, J=8 Hz, H-30); 7.22 (m, 3H, H-24,25 and 26).

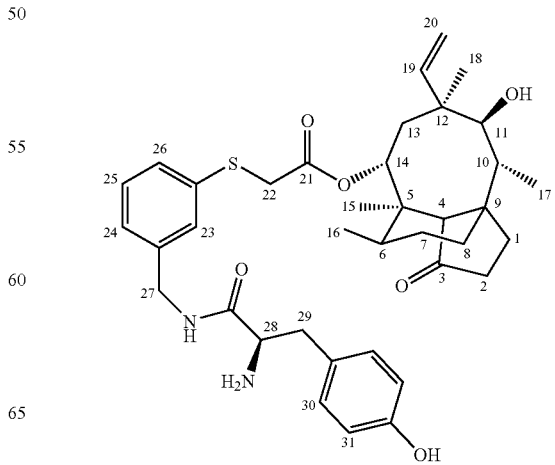

Example 9

14-O-[(3-{[2-Amino-acetylamino]-methyl}-phenyl-sulfanyl)-acetyl]-mutilin hydrochloride ¹H-NMR (400 MHz, DMSO-$d_6$, δ, ppm, characteristic signals): 0.57 (d, 3H, J=7 Hz, $CH_3$-16); 0.79 (d, 3H, J=7 Hz, $CH_3$-17); 0.99 (s, 3H, $CH_3$-18); 1.31 (s, 3H, $CH_3$-15); 2.36 (bs, 1H, H-4); 3.38 (t, 1H, J=6 Hz, H-11); 3.59 (s, 2H, $CH_2$-28); AB-system ($u_A$=3.85, $u_B$=3.78, J=16 Hz, $CH_2$-22); 4.29 (d, 2H, J=6 Hz, $CH_2$-27); 4.95 (m, 2H, H-20); 5.50 (d, 1H, J=8 Hz, H-14); 6.04 (dd, 1H, J=11 and 18 Hz, H-19); 7.11 (m, 1H, H-23); 7.24 (m, 3H, H-24,25 and 26).

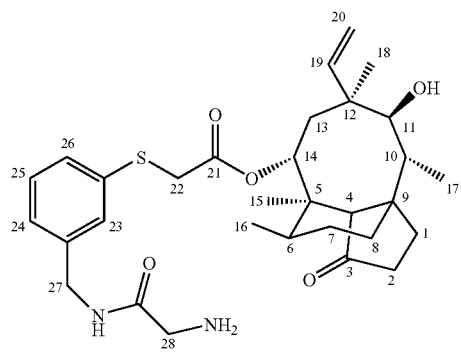

Example 10

14-O-[(3-{[(S)-2-((S)-2-Amino-propionylamino)-propionylamino]-methyl}-phenylsulfanyl)-acetyl]-mutilin hydrochloride ¹H-NMR (400 MHz, DMSO-$d_6$, δ, ppm, characteristic signals): 0.56 (d, 3H, J=7 Hz, $CH_3$-16); 0.79 (d, 3H, J=7 Hz, $CH_3$-17); 0.99 (s, 3H, $CH_3$-18); 1.26 and 1.33 (2×d, 6H, J=7 Hz, $CH_3$-29 and 31); 1.31 (s, 3H, $CH_3$-15); 2.36 (bs, 1H, H-4); 3.37 (t, 1H, J=6 Hz, H-11); AB-system ($u_A$=3.83, $u_B$=3.76, J=16 Hz, $CH_2$-22); 3.84 (m, 1H, H-30); 4.22 (m, 2H, $CH_2$-27); 4.35 (m, 1H, H-28); 4.95 (m, 2H, H-20); 5.50 (d, 1H, J=8 Hz, H-14); 6.03 (m, 1H, H-19); 7.04 (d, 1H, J=7 Hz, H-23); 7.21 (m, 3H, H-24,25 and 26).

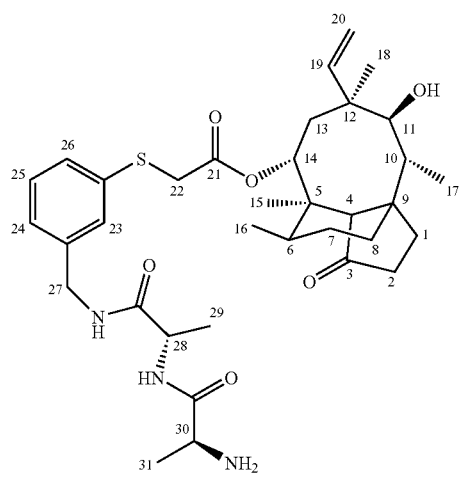

Example 11

14-O-[(3-{[((S)-2-Amino-3-methyl)-butyrylamino]-methyl}-phenylsulfanyl)-acetyl]-mutilin hydrochloride ¹H-NMR (500 MHz, DMSO-$d_6$, δ, ppm, characteristic signals): 0.56 (d, 3H, J=7 Hz, $CH_3$-16); 0.79 (d, 3H, J=7 Hz, $CH_3$-17); 0.91 and 0.92 (2×d, 6H, J=7 Hz, $CH_3$-30); 0.99 (s, 3H, $CH_3$-18); 1.31 (s, 3H, $CH_3$-15); 2.36 (bs, 1H, H-4); 3.37 (t, 1H, J=6 Hz, H-11); 3.60 (m, 1H, H-28); AB-system ($u_A$=3.84, $u_B$=3.77, J=16 Hz, $CH_2$-22); ABX-system ($u_A$=4.34, $u_B$=4.25, $J_{AB}$=15 Hz, $J_{AX}$=6 Hz, $J_{BX}$=6 Hz, $CH_2$-27); 4.95 (m, 2H, H-20); 5.50 (d, 1H, J=8 Hz, H-14); 6.04 (dd, 1H, J=11 and 18 Hz, H-19); 7.12 (d, 1H, J=7 Hz, H-23); 7.24 (m, 3H, H-24,25 and 26).

Example 12

14-O-[(3-{(2-[((R)-Pyrrolidine-2-carbonyl)-amino]-acetylamino)-methyl}-phenylsulfanyl)-acetyl]-mutilin hydrochloride ¹H-NMR (400 MHz, DMSO-$d_6$, δ, ppm, characteristic signals): 0.58 (d, 3H, J=7 Hz, $CH_3$-16); 0.81 (d, 3H, J=7 Hz, $CH_3$-17); 1.01 (s, 3H, $CH_3$-18); 1.33 (s, 3H, $CH_3$-15); 2.38 (bs, 1H, H-4); 3.19 (m, 2H, $CH_2$-32); 3.39 (t, 1H, J=6 Hz, H-11); AB-system ($u_A$=3.89, $u_B$=3.79, J=16 Hz, $CH_2$-22); 3.85 (m, 2H, $CH_2$-28); 4.24 (m, 3H, $CH_2$-27 and H-29); 4.97 (m, 2H, H-20); 5.52 (d, 1H, J=8 Hz, H-14); 6.05 (m, 1H, H-19); 7.08 (m, 1H, H-23); 7.23 (m, 3H, H-24, 25 and 26).

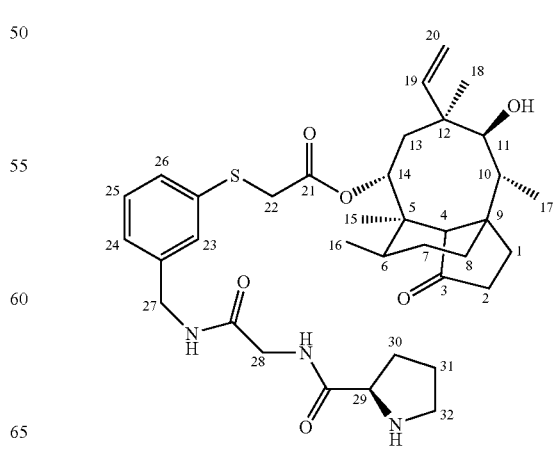

Example 13

14-O-[(3-{[((2R,3S)-2-Amino-3-hydroxy)-butyrylamino]-methyl}-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.11 (d, 3H, J=6 Hz, CH$_3$-30); 1.31 (s, 3H, CH$_3$-15); 2.36 (bs, 1H, H-4); 3.38 (t, 1H, J=6 Hz, H-11); 3.58 (d, 1H, J=6 Hz, H-28); AB-system (u$_A$=3.84, u$_B$=3.78, J=16 Hz, CH$_2$-22); 3.91 (m, 1H, H-29); 4.30 (m, 2H, CH$_2$-27); 4.95 (m, 2H, H-20); 5.51 (d, 1H, J=8 Hz, H-14); 6.04 (dd, 1H, J=11 and 18 Hz, H-19); 7.12 (d, 1H, J=7 Hz, H-23); 7.25 (m, 3H, H-24,25 and 26).

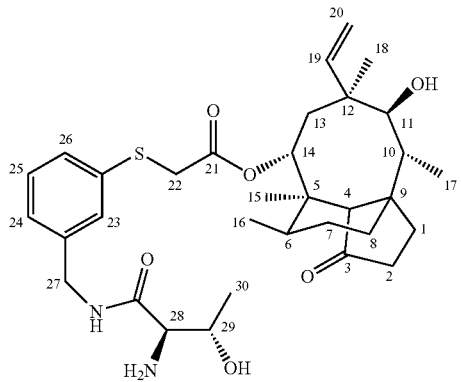

Example 14

14-O-[(3-{[(R)-2,6-Diamino-hexanoylamino]-methyl}-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); 2.72 (m, 2H, CH$_2$-32); 3.38 (t, 1H, J=6 Hz, H-11); AB-system (u$_A$=3.86, u$_B$=3.78, J=16 Hz, CH$_2$-22); 3.79 (m, 1H, H-28); ABX-system (u$_A$=4.33, u$_B$=4.25, J$_{AB}$=15 Hz, J$_{AX}$=6 Hz, J$_{BX}$=6 Hz, CH$_2$-27); 4.95 (m, 2H, H-20); 5.50 (d, 1H, J=8 Hz, H-14); 6.05 (dd, 1H, J=11 and 18 Hz, H-19); 7.11 (d, 1H, J=7 Hz, H-23); 7.25 (m, 3H, H-24,25 and 26).

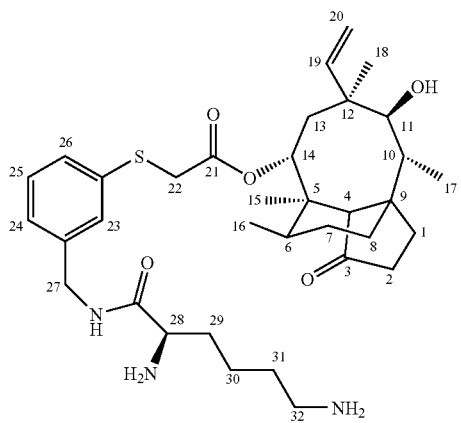

Example 15

14-O-[(3-{[(R)-2-Amino-3-(1H-indol-3-yl)-propylamino]-methyl}-phenylsulfanyl)-acetyl]-mutilin hydrochloride $^1$H-NMR (400 MHz, DMSO-d$_6$, δ, ppm, characteristic signals): 0.55 (d, 3H, J=7 Hz, CH$_3$-16); 0.78 (d, 3H, J=7 Hz, CH$_3$-17); 0.99 (s, 3H, CH$_3$-18); 1.31 (s, 3H, CH$_3$-15); 2.35 (bs, 1H, H-4); ABX-system (u$_A$=3.23, u$_B$=3.12, J$_{AB}$=15 Hz, J$_{AX}$=6 Hz, J$_{gx}$=8 Hz, CH$_2$-29); 3.38 (t, 1H, J=6 Hz, H-11); AB-system (u$_A$=3.83, u$_B$=3.76, J=16 Hz, CH$_2$-22); 4.00 (t, 1H, J=7 Hz, H-28); 4.23 (m, 2H, CH$_2$-27); 4.94 (m, 2H, H-20); 5.50 (d, 1H, J=8 Hz, H-14); 6.04 (dd, 1H, J=11 and 18 Hz, H-19); 6.89 (m, 1H, H-23); 6.99 and 7.08 (2xt, 2H, J=7 Hz, H-32 and 33); 7.18 (m, 4H, H-24,25,26 and 30); 7.36 and 7.65 (2xd, 2H, J=8 Hz, H-31 and 34).

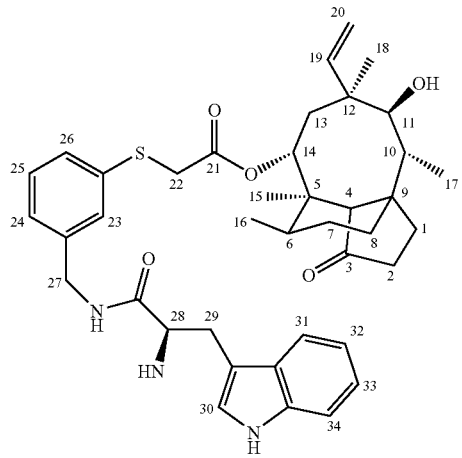

Example 16

14-O-[(3-{[(R)-2-Amino-3-phenyl-propionylamino]-methyl}-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); 3.03 (m, 2H, CH$_2$-29); 3.37 (t, 1H, J=6 Hz, H-11); AB-system (u$_A$=3.83, u$_B$=3.76, J=16 Hz, CH$_2$-22); 4.01 (m, 1H, H-28); ABX-system (u$_A$=4.26, u$_B$=4.17, J$_{AB}$=15 Hz, J$_{AX}$=6 Hz, J$_{BX}$=5 Hz, CH$_2$-27); 4.95 (m, 2H, H-20); 5.50 (d, 1H, J=8 Hz, H-14); 6.04 (dd, 1H, J=11 and 18 Hz, H-19); 6.86 (m, 1H, H-23); 7.18 and 7.27 (2xm, 8H, H-24,25,26,30, 31 and 32).

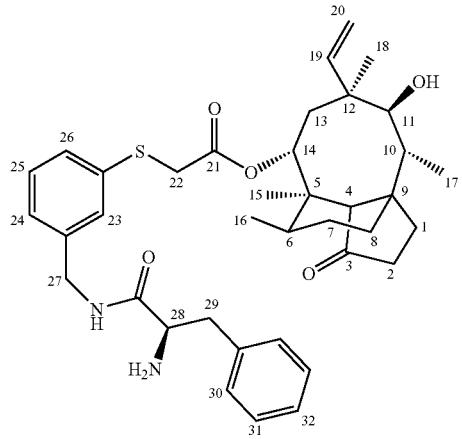

Example 17

14-O-[(3-{[(R)-2-Amino-3-carbamoyl-propionylamino]-methyl}-phenylsulfanyl)-acetyl]-mutilin hydrochloride $^1$H-NMR (400 MHz, DMSO-d$_6$, δ, ppm, characteristic signals): 0.57 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); ABX-system (u$_A$=2.71, u$_B$=2.63, J$_{AB}$=17 Hz, J$_{AX}$=5 Hz, J$_{BX}$=8 Hz, CH$_2$-29); 3.38 (t, 1H, J=6 Hz, H-11); AB-system (u$_A$=3.85, u$_B$=3.78, J=16 Hz, CH$_2$-22); 4.07 (dd, 1H, J=5 and 8 Hz, H-28); 4.28 (m, 2H, CH$_2$-27); 4.95 (m, 2H, H-20); 5.51 (d, 1H, J=8 Hz, H-14); 6.04 (dd, 1H, J=11 and 18 Hz, H-19); 7.09 (d, 1H, J=7 Hz, H-23); 7.22 (m, 3H, H-24,25 and 26).

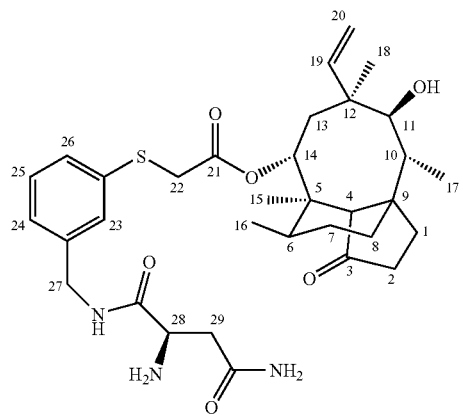

Example 18

14-O-[(3-{[(S)-2,6-Diamino-hexanoylamino]-methyl}-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); 2.73 (t, 2H, J=8 Hz, CH$_2$-32); 3.38 (t, 1H, J=6 Hz, H-11); AB-system (u$_A$=3.85, u$_B$=3.78, J=16 Hz, CH$_2$-22); 3.80 (m, 1H, H-28); ABX-system (u$_A$=4.33, u$_B$=4.25, J$_{AB}$=15 Hz, J$_{AX}$=6 Hz, J$_{BX}$=6 Hz, CH$_2$-27); 4.95 (m, 2H, H-20); 5.50 (d, 1H, J=8 Hz, H-14); 6.05 (dd, 1H, J=11 and 18 Hz, H-19); 7.11 (d, 1H, J=7 Hz, H-23); 7.23 (m, 3H, H-24,25 and 26).

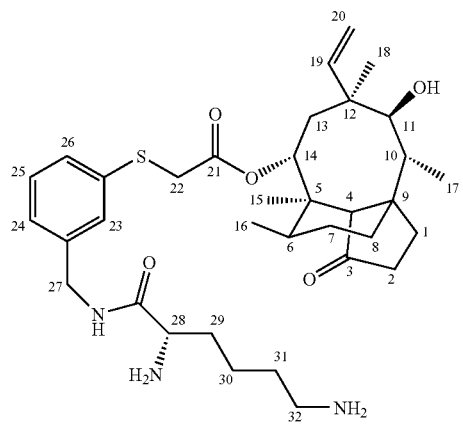

Example 19

14-O-[(3-{[(S)-2-((S)-2-Amino-4-methyl-pentanoylamino)-4-methyl-pentanoylamino]-methyl}-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.82-0.88 (4×d, 12H, J=7 Hz, CH$_3$-31 and 35); 0.99 (s, 3H, CH$_3$-18); 1.31 (s, 3H, CH$_3$-15); 2.36 (bs, 1H, H-4); 3.39 (t, 1H, J=6 Hz, H-11); AB-system (u$_A$=3.82, u$_B$=3.75, J=15 Hz, CH$_2$-22); 3.77 (m, 1H, H-32); 4.20 (m, 2H, CH$_2$-27); 4.38 (m, 1H, H-28); 4.95 (m, 2H, H-20); 5.50 (d, 1H, J=8 Hz, H-14); 6.05 (dd, 1H, J=11 and 18 Hz, H-19); 7.00 (m, 1H, H-23); 7.22 (m, 3H, H-24,25 and 26).

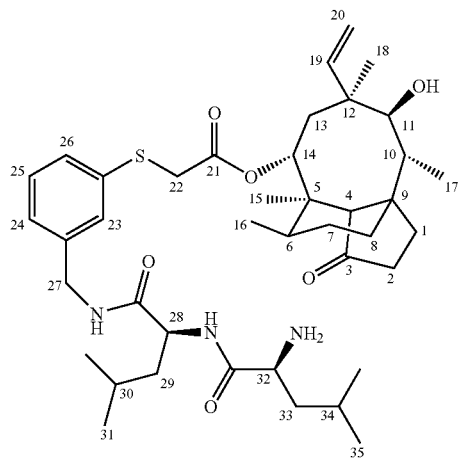

Example 20

14-O-[(3-{[((R)-2-Amino-3-hydroxy)-propionylamino]-4-methyl}-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); 3.38 (t, 1H, J=6 Hz, H-11); 3.75 (m, 2H, CH$_2$-29); 3.84 (m, 1H, H-28); AB-system (u$_A$=3.84, u$_B$=3.78, J=16 Hz, CH$_2$-22); 4.29 (m, 2H, CH$_2$-27); 4.95 (m, 2H, H-20); 5.50 (d, 1H, J=8 Hz, H-14); 6.04 (m, 1H, H-19); 7.10 (d, 1H, J=7 Hz, H-23); 7.22 (m, 3H, H-24,25 and 26).

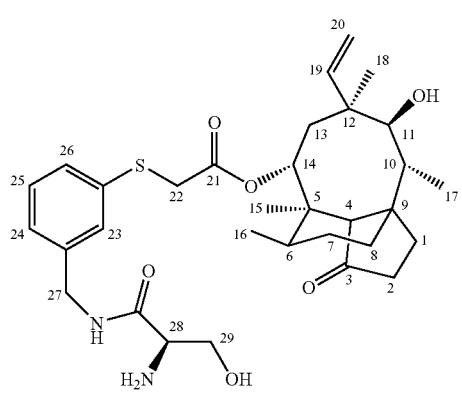

Example 21

14-O-[(3-{[(S)-2-Amino-propylamino]-methyl}-phenylsulfanyl)-acetyl]-mutilin hydrochloride $^1$H-NMR (400 MHz, DMSO-$d_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 1.37 (d, 3H, J=7 Hz, CH$_3$-29); 2.36 (bs, 1H, H-4); 3.38 (t, 1H, J=6 Hz, H-11); AB-system (u$_A$=3.84, u$_B$=3.77, J=16 Hz, CH$_2$-22); 3.86 (m, 1H, H-28); 4.28 (d, 2H, J=6 Hz, CH$_2$-27); 4.95 (m, 2H, H-20); 5.50 (d, 1H, J=8 Hz, H-14); 6.04 (dd, 1H, J=11 and 18 Hz, H-19); 7.08 (d, 1H, J=7 Hz, H-23); 7.22 (m, 3H, H-24,25 and 26).

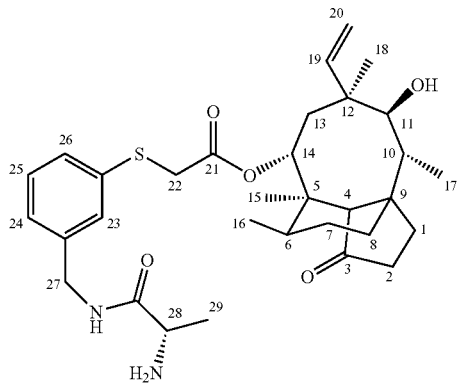

Example 22

14-O-[(3-{[(R)-2-Amino-4-carbamoyl-butyrylamino]-methyl}-phenylsulfanyl)-acetyl]-mutilin hydrochloride $^1$H-NMR (500 MHz, DMSO-$d_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); 3.38 (t, 1H, J=6 Hz, H-11); AB-system (u$_A$=3.84, u$_B$=3.78, J=16 Hz, CH$_2$-22); 3.82 (m, 1H, H-28); ABX-system (u$_A$=4.35, u$_B$=4.23, J$_{AB}$=15 Hz, J$_{AX}$=6 Hz, J$_{BX}$=5 Hz, CH$_2$-27); 4.95 (m, 2H, H-20); 5.50 (d, 1H, J=8 Hz, H-14); 6.04 (dd, 1H, J=11 and 18 Hz, H-19); 7.11 (m, 1H, J=7 Hz, H-23); 7.24 (m, 3H, H-24,25 and 26).

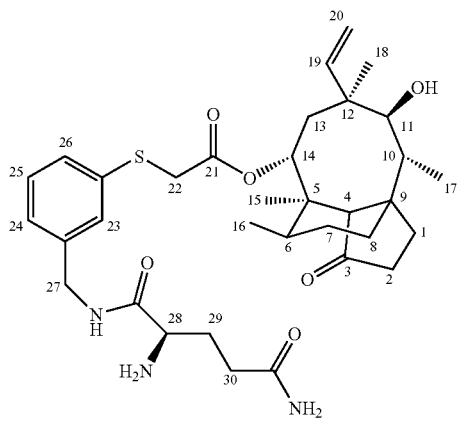

Example 23

14-O-[(3-{[(S)-1-(2-Amino-acetyl)-pyrrolidine-2-carbonyl)-amino]-methyl}-phenylsulfanyl)-acetyl]-mutilin hydrochloride $^1$H-NMR (500 MHz, DMSO-$d_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); 3.38 (t, 1H, J=6 Hz, H-11); 3.45 and 3.56 (2×m, 2H, CH$_2$-30); AB-system (u$_A$=3.83, u$_B$=3.76, J=16 Hz, CH$_2$-22); 3.78 (m, 2H, CH$_2$-32); ABX-system (u$_A$=4.26, u$_B$=4.16, J$_{AB}$=15 Hz, J$_{AX}$=6 Hz, J$_{BX}$=6 Hz, CH$_2$-27); 4.36 (m, 1H, H-28); 4.95 (m, 2H, H-20); 5.50 (d, 1H, J=8 Hz, H-14); 6.04 (dd, 1H, J=11 and 17 Hz, H-19); 7.07 (d, 1H, J=7 Hz, H-23); 7.21 (m, 3H, H-24,25 and 26).

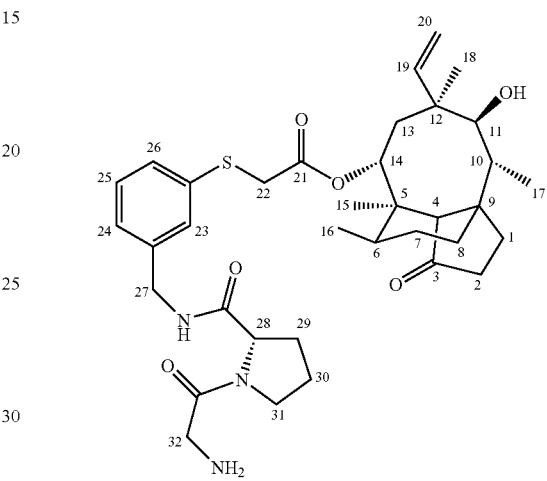

Example 24

14-O-[(3-{[(R)-2-Amino-3-(3H-imidazol-4-yl)-propionylamino]-methyl}-phenylsulfanyl)-acetyl]-mutilin hydrochloride $^1$H-NMR (400 MHz, DMSO-$d_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); ABX-system (u$_A$=3.27, u$_B$=3.19, J$_{AB}$=17 Hz, J$_{AX}$=6 Hz, J$_{BX}$=7 Hz, CH$_2$-29); 3.37 (t, 1H, J=6 Hz, H-11); AB-system (u$_A$=3.85, u$_B$=3.78, J=16 Hz, CH$_2$-22); 4.24 (m, 3H, CH$_2$-27 and H-28); 4.95 (m, 2H, H-20); 5.50 (d, 1H, J=8 Hz, H-14); 6.04 (dd, 1H, J=11 and 18 Hz, H-19); 6.98 (m, 1H, H-23); 7.22 (m, 3H, H-24,25 and 26); 7.44 (s, 1H, H-30); 9.00 (s, 1H, H-31).

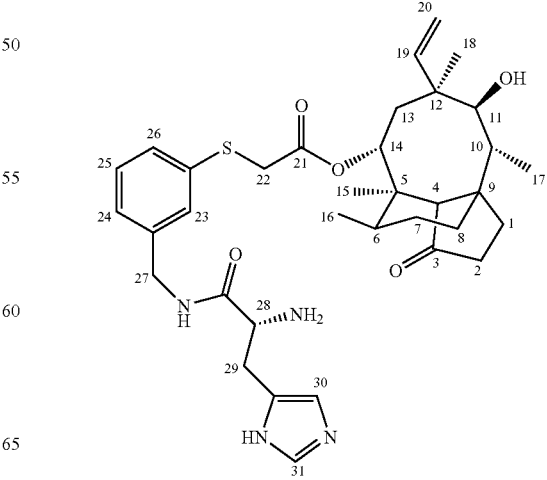

Example 25

14-O-[(3-{[((2S,4R)-4-Hydroxy-pyrrolidine-2-carbonyl)-amino]-methyl}-phenylsulfanyl)-acetyl]-mutilin hydrochloride

$^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); AB-system (u$_A$=3.38, u$_B$=3.07, J=12 Hz, CH$_2$-31); 3.38 (t, 1H, J=6 Hz, H-11); AB-system (u$_A$=3.85, u$_B$=3.78, J=16 Hz, CH$_2$-22); 4.27-4.46 (3×m, 4H, CH$_2$-27, H-28 and 30); 4.96 (m, 2H, H-20); 5.50 (d, 1H, J=8 Hz, H-14); 6.04 (m, 1H, H-19); 7.08 (d, 1H, J=7 Hz, H-23); 7.23 (m, 3H, H-24,25 and 26).

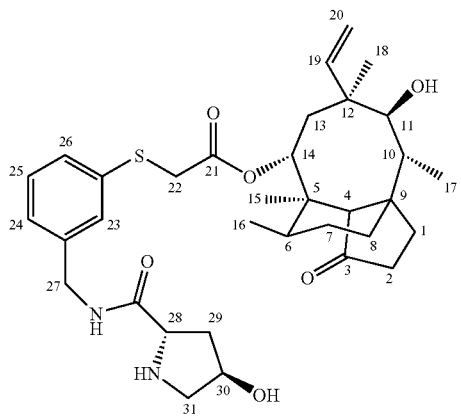

Example 26

14-O-[(3-{[(S)-Piperidine-2-carbonyl)-amino]-methyl}-phenylsulfanyl)-acetyl]-mutilin hydrochloride

$^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18), 1.31 (s, 3H, CH$_3$-15); 2.36 (bs, 1H, H-4); 2.89 and 3.19 (2×m, 2H, CH$_2$-32); 3.38 (t, 1H, J=6 Hz, H-11); AB-system (u$_A$=3.85, u$_B$=3.78, J=16 Hz, CH$_2$-22); 3.78 (bm, 1H, H-28); 4.29 (d, 2H, J=6 Hz, CH$_2$-27); 4.96 (m, 2H, H-20); 5.50 (d, 1H, J=8 Hz, H-14); 6.04 (dd, 1H, J=11 and 18 Hz, H-19); 7.08 (m, 1H, H-23); 7.23 (m, 3H, H-24,25 and 26).

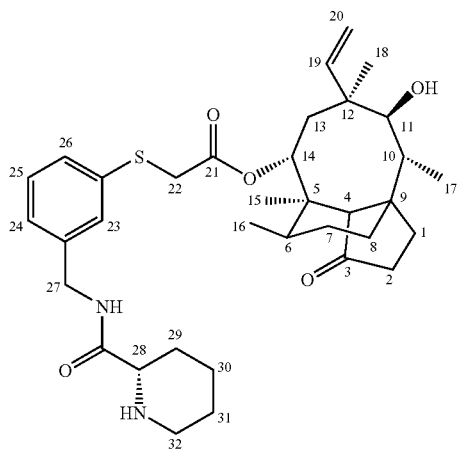

Example 27

14-O-[(3-{[((S)-Pyrrolidine-2-carbonyl)-amino]-methyl}-phenylsulfanyl)-acetyl]-mutilin hydrochloride

$^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); 3.29 (m, 2H, CH$_2$-31); 3.37 (t, 1H, J=6 Hz, H-11); AB-system (u$_A$=3.84, u$_B$=3.76, J=16 Hz, CH$_2$-22); 4.19 (m, 1H, H-28); 4.30 (m, 2H, CH$_2$-27); 4.95 (m, 2H, H-20); 5.50 (d, 1H, J=8 Hz, H-14); 6.04 (m, 1H, H-19); 7.09 (d, 1H, J=7 Hz, H-23); 7.24 (m, 3H, H-24,25 and 26).

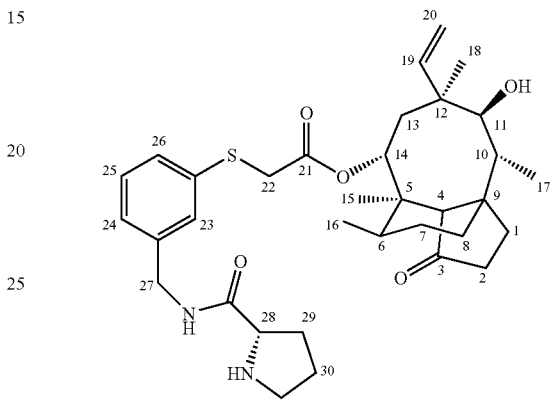

Example 28

14-O-[(3-{[(S)-2-Amino-3-(4-hydroxy-phenyl)-propionylamino]-methyl}-phenylsulfanyl)-acetyl]-mutilin hydrochloride

$^1$H-NMR (400 MHz, DMSO-d$_6$, δ, ppm, characteristic signals): 0.56 (d, 3H, J=7 Hz, CH$_3$-16); 0.78 (d, 3H, J=7 Hz, CH$_3$-17); 0.99 (s, 3H, CH$_3$-18); 1.31 (s, 3H, CH$_3$-15); 2.36 (bs, 1H, H-4); ABX-system u$_A$=2.95, u$_B$=2.88, J$_{AB}$=15 Hz, J$_{AX}$=7 Hz, J$_{BX}$=7 Hz, CH$_2$-29); 3.37 (t, 1H, J=6 Hz, H-11); AB-system (u$_A$=3.83, u$_B$=3.76, J=16 Hz, CH$_2$-22); 3.92 (t, 1H, J=7 Hz, H-28); ABX-system (u$_A$=4.27, u$_B$=4.19, J$_{AB}$=15 Hz, J$_{AX}$=6 Hz, J$_{BX}$=6 Hz, CH$_2$-27); 4.95 (m, 2H, H-20); 5.50 (d, 1H, J=8 Hz, H-14); 6.04 (dd, 1H, J=11 and 18 Hz, H-19); 6.68 (d, 2H, J=8 Hz, H-31); 6.85 (m, 1H, H-23); 6.99 (d, 2H, J=8 Hz, H-30); 7.22 (m, 3H, H-24,25 and 26).

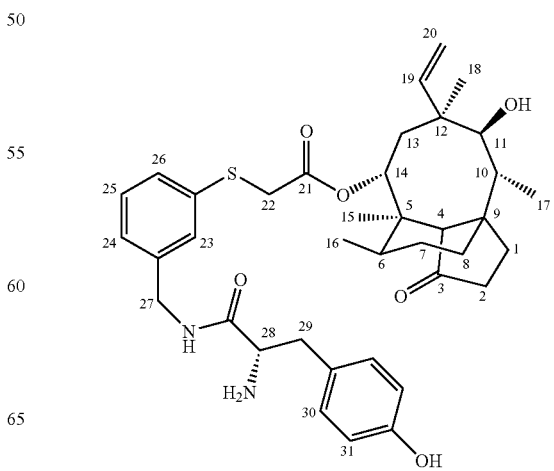

Example 29

14-O-[(3-{[(S)-2-Amino-3-phenyl-propionylamino]-methyl}-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); 3.03 (m, 2H, CH$_2$-29); 3.37 (t, 1H, J=6 Hz, H-11); AB-system (u$_A$=3.83, u$_B$=3.77, J=16 Hz, CH$_2$-22); 4.00 (t, 1H, J=7 Hz, H-28); ABX-system (u$_A$=4.27, u$_B$=4.17, J$_{AB}$=15 Hz, J$_{AX}$=6 Hz, J$_{BX}$=6 Hz, CH$_2$-27); 4.95 (m, 2H, H-20); 5.50 (d, 1H, J=8 Hz, H-14); 6.04 (dd, 1H, J=11 and 18 Hz, H-19); 6.86, (m, 1H, H-23); 7.17 and 7.27 (2×m, 8H, H-24,25,26,30,31 and 32).

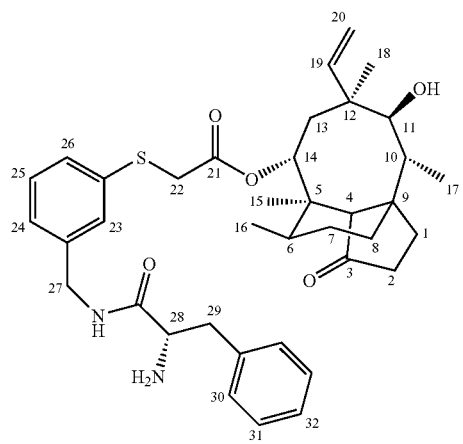

Example 30

14-O-[(3-{[((S)-2-Amino-3-hydroxy)-propionylamino]-methyl}-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.31 (s, 3H, CH$_3$-15); 2.36 (bs, 1H, H-4); 3.38 (t, 1H, J=6 Hz, H-11); 3.73 (m, 3H, CH$_2$-29); 3.84 (m, 1H, H-28); AB-system (u$_A$=3.84, u$_B$=3.77, J=16 Hz, CH$_2$-22); 4.29 (m, 2H, CH$_2$-27); 4.95 (m, 2H, H-20); 5.50 (d, 1H, J=8 Hz, H-14); 6.04 (m, 1H, H-19); 7.10 (d, 1H, J=7 Hz, H-23); 7.22 (m, 3H, H-24,25 and 26).

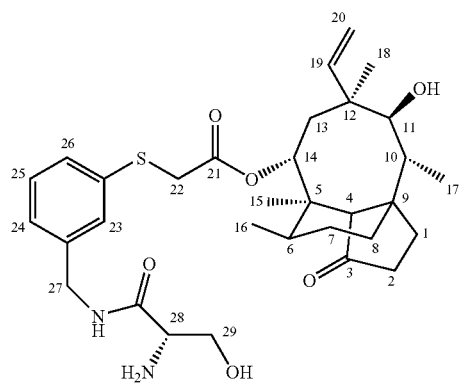

Example 31

14-O-[(3-{[((2S,3R)-2-Amino-3-hydroxy)-butyrylamino]-methyl}-phenylsulfanyl)-acetyl]-mutilin hydrochloride $^1$H-NMR (400 MHz, DMSO-d$_6$, δ, ppm, characteristic signals): 0.56 (d, 3H, J=7 Hz, CH$_3$-16); 0.79 (d, 3H, J=7 Hz, CH$_3$-17); 0.99 (s, 3H, CH$_3$-18); 1.13 (d, 3H, J=6 Hz, CH$_3$-30); 1.31 (s, 3H, CH$_3$-15); 2.36 (bs, 1H, H-4); 3.38 (t, 1H, J=6 Hz, H-11); 3.58 (d, 1H, J=6 Hz, H-28); AB-system (u$_A$=3.84, u$_B$=3.77, J=16 Hz, CH$_2$-22); 3.89 (m, 1H, H-29); 4.29 (m, 2H, CH$_2$-27); 4.95 (m, 2H, H-20); 5.50 (d, 1H, J=8 Hz, H-14); 6.04 (m, 1H, H-19); 7.12 (bd, 1H, J=7 Hz, H-23); 7.25 (m, 3H, H-24,25 and 26).

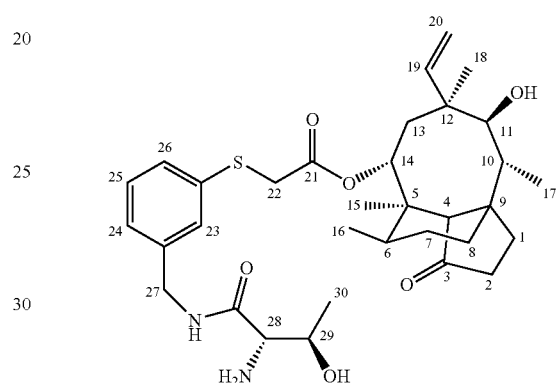

Example 32

14-O-[(3-{[((R)-2-Amino-3-hydroxy)-propionylamino]-methyl}-phenoxy)-acetyl]-mutilin hydrochloride Step 1: 14-O-[(3-Hydroxymethyl-phenoxyacetyl]-mutilin To 1.42 g (56.4 mmol) of sodium hydride in 150 mL of DMF 7 g (56.4 mmol) of 3-Hydroxymethyl-phenol in 80 mL of DMF is added at room temperature. After stirring the reaction for 30 min at 30° C. a solution of 30 g (56.4 mmol) of Pleuromutilintosylate in 130 mL of acetone is added and the reaction stirred at ambient temperature for 2 h. The reaction mixture is evaporated to dryness under reduced pressure, dissolved in ethyl acetate and extracted three times with water. The organic phase is dried with Na$_2$SO$_4$, evaporated to dryness under reduced pressure and the residue is chromatographed on silica gel using dichloromethane/methanol 100:2 as mobile phase.

$^1$H-NMR (400 MHz, DMSO-d$_6$, δ, ppm, characteristic signals): 0.64 (d, 3H, J=7 Hz, CH$_3$-16); 0.81 (d, 3H, J=7 Hz, CH$_3$-17); 1.04 (s, 3H, CH$_3$-18); 1.34 (s, 3H, CH$_3$-15); 2.40 (s, 1H, H-4); 3.41 (t, 1H, J=6 Hz, H-11); 4.40 (m, 2H, CH$_2$-27); AB-system (u$_A$=4.74, u$_B$=4.62, J=17 Hz, CH$_2$-22); 5.04 (m, 2H, H-20); 5.08 (m, 1H, H-14); 6.11 (dd, 1H, J=11 and 18 Hz, H-19), 6.73 (dd, 1H, J=2 and 8 Hz, H-26); 6.80 (bs, 1H, H-23); 6.92 (d, 1H, J=8 Hz, H-24 and 26); 7.19 (m, 1H, H-25).

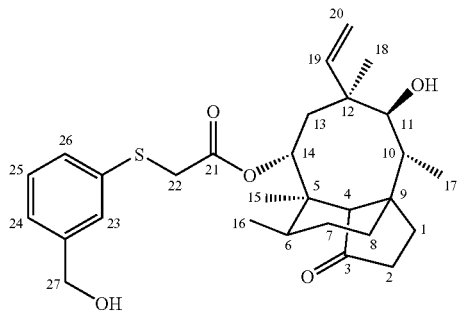

Step 2: 14-O-[(3-Methanesulfonyloxymethyl-phenoxy)-acetyl]-mutilin

To 23 g (47.5 mmol) of 14-O-[3-Hydroxymethyl-phenoxyacetyl]-mutilin in 400 mL of dry THF and 8.88 mL (80.8 mmol) of N-methylmorpholine together with a catalytic amount of 4-dimethylaminopyridine 14.42 g (82.8 mmol) of methanesulfonic anhydride in 80 mL of dry THF is added at +4° C. The reaction mixture is allowed to stir for 1 h at ambient temperature. After addition of water the mixture is extracted with ethyl acetate and then the organic phase washed several times with water and brine. The organic phase is dried with anhydrous sodium sulfate, concentrated under reduced pressure and chromatographed on silica gel using dichloromethane/methanol 100:1 as mobile phase.

$^1$H-NMR (400 MHz, DMSO, δ, ppm, characteristic signals): 0.64 (d, 3H, J=7 Hz, $CH_3$-16); 0.81 (d, 3H, J=7 Hz, $CH_3$-17); 1.04 (s, 3H, $CH_3$-18); 1.34 (s, 3H, $CH_3$-15); 2.40 (bs, 1H, H-4); 3.20 (s, 3H, $CH_3$-28); 3.39 (t, 1H, J=6 Hz, H-11); AB-system ($u_A$=4.76, $u_B$=4.68, J=16 Hz, $CH_2$-22); 5.01 and 5.07 (2×dd, 2H, J=2 and 11 Hz; J=2 and 18 Hz, H-20); 5.60 (d, 1H, J=8 Hz, H-14); 6.11 (dd, 1H, J=11 and 17 Hz, H-19); 6.92 (dd, 1H, J=2 and 8 Hz, H-26); 6.98 (d, 1H, J=2 Hz, H-23); 7.03 (d, 1H, J=8 Hz, H-24); 7.31 (t, 1H, J=8 Hz, H-25).

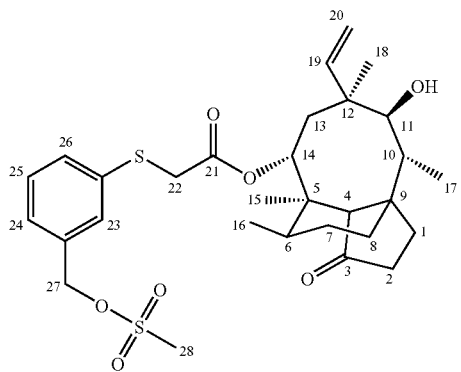

Step 3: 14-O-[(3-Azidomethyl-phenoxy)-acetyl]-mutilin

To 8.14 g (14.5 mmol) of 14-O-[(3-Methanesulfonyloxymethyl-phenoxy)-acetyl]-mutilin in 80 mL of DMF 3.77 g (58 mmol) of $NaN_3$ is added. The resulting suspension is stirred for 4.5 h at 50° C. and left overnight at ambient temperature. Water and ethyl acetate are added and the organic phase washed several times with water and brine. After concentrating under reduced pressure, the residue is chromatographed on silica using $CH_2Cl_2$/MeOH 100:1 as mobile phase.

$^1$H-NMR (400 MHz, DMSO-$d_6$, δ, ppm, characteristic signals): 0.64 (d, 3H, J=7 Hz, $CH_3$-16); 0.81 (d, 3H, J=7 Hz, $CH_3$-17); 1.04 (s, 3H, $CH_3$-18); 1.33 (s, 3H, $CH_3$-15); 2.41 (bs, 1H, H-4); 3.41 (t, 1H, J=6 Hz, H-11); 4.38 (m, 2H, $CH_2$-27); AB-system ($u_A$=4.74, $u_B$=4.68, J=17 Hz, $CH_2$-22); 5.03 (m, 2H, H-20); 5.60 (d, 1H, J=8 Hz, H-14); 6.11 (dd, 1H, J=11 and 18 Hz, H-19); 6.88 (dd, 1H, J=2 and 8 Hz, H-26); 6.90 (bs, 1H, H-23); 6.95 (d, 1H, J=8 Hz, H-24); 7.29 (t, 1H, J=8 Hz, H-25).

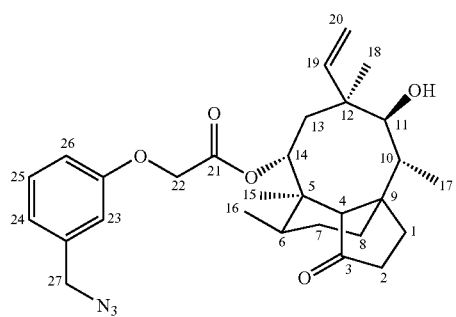

Step 4: 14-O-[(3-Aminomethyl-phenoxy)-acetyl]-mutilin hydrochloride 5.6 g (11 mmol) of 14-O-[(3-Azidomethyl-phenoxy)-acetyl]-mutilin is dissolved in 170 mL of THF, 5.1 g of Lindlar-catalyst is added and the reaction mixture hydrogenated for 30 minutes. The reaction mixture is filtered through celite, concentrated under reduced pressure and the residue is chromatographed on silica using $CH_2Cl_2$/MeOH 10:1 as mobile phase.

$^1$H-NMR (400 MHz, DMSO-$d_6$, δ, ppm, characteristic signals): 0.64 (d, 3H, J=7 Hz, $CH_3$-16); 0.81 (d, 3H, J=7 Hz, $CH_3$-17); 1.04 (s, 3H, $CH_3$-18), 1.34 (s, 3H, $CH_3$-15); 2.40 (bs, 1H, H-4); 3.42 (t, 1H, J=6 Hz, H-11); 3.64 (s, 2H, $CH_2$-27); AB-system ($u_A$=4.69, $u_B$=4.62, J=17 Hz, $CH_2$-22); 5.01 and 5.07 (2×dd, 2H, J=2 and 11 Hz; J=2 and 18 Hz, H-20); 5.60 (d, 1H, J=8 Hz, H-14); 6.11 (dd, 1H, J=11 and 18 Hz, H-19); 6.70 (dd, 1H, J=2 and 8 Hz; H-26); 6.86 (d, 1H, J=2 Hz, H-23); 6.89 (d, 1H, J=8 Hz, H-24); 7.16 (t, 1H, J=8 Hz, H-25).

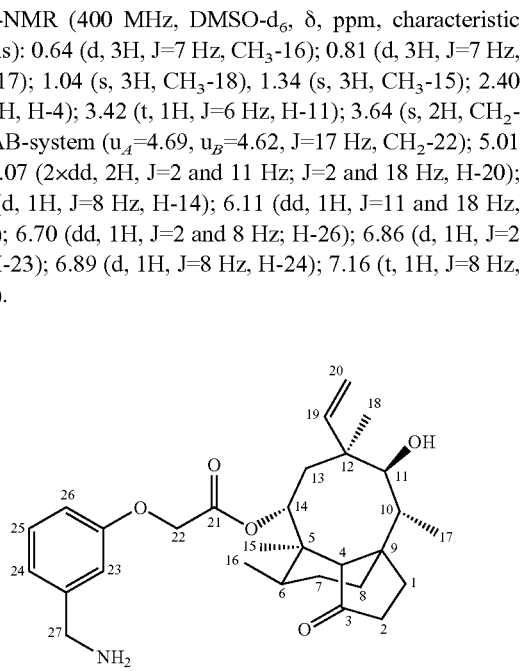

The hydrochloride was obtained by dissolving 125 mg of 14-O-[(3-Aminomethyl)-phenylsulfanyl-acetyl]-mutilin in 3 mL of $CH_2Cl_2$ and adding 2 mL of HCl-saturated $Et_2O$. After 45 minutes the reaction was evaporated to dryness under reduced pressure.

Step 5: 14-O-[(3-{[((R)-2-tert-Butoxycarbonylamino-3-hydroxy)-propionylamino]-methyl}-phenoxy)-acetyl]-mutilin To 300 mg (0.62 mmol) of 14-O-[(3-Aminomethyl-phenoxy)-acetyl]mutilin in 6 mL of THF is added 207 mg (0.96 mmol) of BOC-D-Proline together with 198 mg (0.96 mmol) of DCC and 75 mg (0.62 mmol) of DMAP. The reaction is stirred for 3 h at ambient temperature, the formed precipitate is filtered off and the filtrate is evaporated to dryness under reduced pressure. The residue is chromatographed on silica using dichloromethane/methanol 100:4 as mobile phase.

$^1$H-NMR (400 MHz, DMSO-d$_6$, δ, ppm, characteristic signals): 0.64 (d, 3H, J=7 Hz, CH$_3$-16); 0.81 (d, 3H, J=7 Hz, CH$_3$-17); 1.05 (s, 3H, CH$_3$-18); 1.34 (s, 3H, CH$_3$-15); 1.37 (s, 9H, CH$_3$-30); 2.40 (bs, 1H, H-4); 3.41 (t, 1H, J=6 Hz, H-11); 3.56 (m, 2H, CH$_2$-29); 3.98 (m, 1H, H-28); ABX-system (u$_A$=4.26, u$_B$=4.19, J$_{AB}$=16 Hz, J$_{AX}$=6 Hz, J$_{BX}$=6 Hz, CH$_2$-27); (AB-system (u$_A$=4.68, u$_B$=4.64, J=17 Hz, CH$_2$-22); 5.01 and 5.07 (2×dd, 2H, J=2 and 11 Hz; J=2 and 18 Hz, H-20); 5.61 (d, 1H, J=8 Hz, H-14); 6.12 (dd, 1H, J=11 and 18 Hz, H-19); 6.72 (dd, 1H, J=2 and 8 Hz, H-26); 6.79 (bs, 1H, H-23); 6.83 (d, 1H, J=8 Hz, H-24); 7.16 (t, 1H, J=8 Hz, H-25).

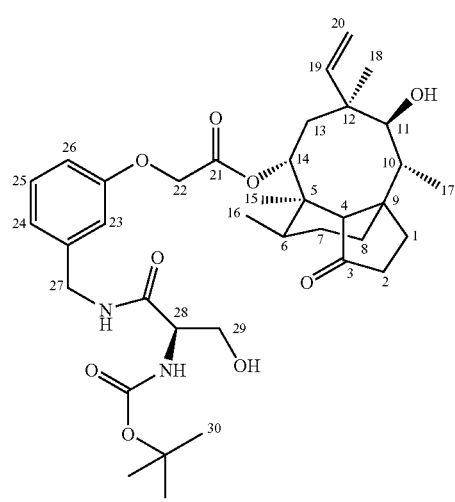

Step 6: 14-O-[(3-{[((R)-2-Amino-3-hydroxy)-propionylamino]-methyl}-phenoxy)-acetyl]-mutilin hydrochloride 173 mg (0.28 mmol) of 14-O-[(3-{[((R)-2-tert-Butoxycarbonylamino-3-hydroxy)-propionylamino]-methyl}-phenoxy)-acetyl]-mutilin is dissolved in 2 mL of dichloromethane and 5 mL of HCl-saturated Et$_2$O was added. The reaction was left at ambient temperature for 3 h and evaporated to dryness under reduced pressure.

$^1$H-NMR (400 MHz, DMSO-d$_6$, δ, ppm, characteristic signals): 0.64 (d, 3H, J=7 Hz, CH$_3$-16); 0.81 (d, 3H, J=7 Hz, CH$_3$-17); 1.05 (s, 3H, CH$_3$-18), 1.35 (s, 3H, CH$_3$-15); 2.40 (bs, 1H, H-4); 3.41 (t, 1H, J=6 Hz, H-11); 3.76 (m, 2H, CH$_2$-29); 3.84 (dd, 1H, J=4 and 6 Hz, H-28); ABX-system (u$_A$=4.32, u$_B$=4.26, J$_{AB}$=16 Hz, J$_{AX}$=6 Hz, J$_{BX}$=6 Hz, CH$_2$-27); AB-system (u$_A$=4.71, u$_B$=4.62, J=17 Hz, CH$_2$-22); 5.01 and 5.07 (2×dd, 2H, J=2 and 11 Hz; J=2 and 18 Hz, H-20); 5.60 (d, 1H, J=8 Hz, H-14); 6.11 (dd, 1H, J=11 and 18 Hz, H-19); 6.76 (dd, 1H, J=2 and 8 Hz, H-26); 6.84 (bs, 1H, H-23); 6.87 (d, 1H, J=8 Hz, H-24); 7.21 (t, 1H, J=8 Hz, H-25).

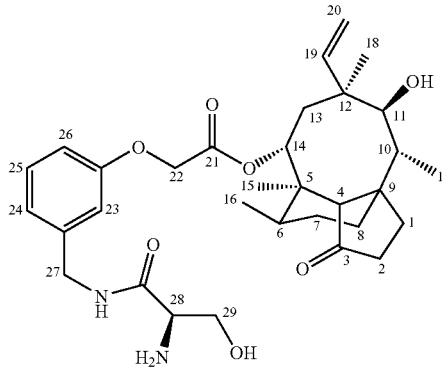

The following compounds are prepared in a similar fashion:

Example 33

14-O-[(3-{[((R)-Pyrrolidine-2-carbonyl)-amino]-methyl}-phenoxy)-acetyl]-mutilin hydrochloride $^1$H-NMR (400 MHz, DMSO-d$_6$, δ, ppm, characteristic signals): 0.63 (d, 3H, J=7 Hz, CH$_3$-16); 0.81 (d, 3H, J=7 Hz, CH$_3$-17); 1.05 (s, 3H, CH$_3$-18), 1.34 (s, 3H, CH$_3$-15); 2.40 (bs, 1H, H-4); 3.18 (m, 2H, CH$_2$-31); 3.41 (d, 1H, J=6 Hz, H-11); 4.18 (m, 1H, H-28); 4.28 (m, 2H, CH$_2$-27); AB-system (u$_A$=4.72, u$_B$=4.63, J=17 Hz, CH$_2$-22); 5.01 and 5.07 (2×dd, 2H, J=2 and 11 Hz; J=2 and 18 Hz, H-20); 5.60 (d, 1H, J=8 Hz, H-14); 6.11 (dd, 1H, J=11 and 18 Hz, H-19); 6.77 (dd, 1H, J=2 and 8 Hz; H-26); 6.83 (bs, 1H, H-23); 6.86 (d, 1H, J=8 Hz, H-24); 7.22 (t, 1H, J=8 Hz, H-25).

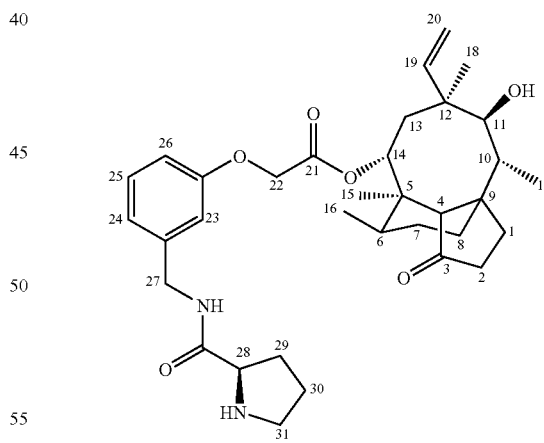

Example 34

14-O-[(3-{[(S)-2-Amino-3-(4-hydroxy-phenyl)-propionylamino]-methyl}-phenoxy)-acetyl]-mutilin hydrochloride $^1$H-NMR (400 MHz, DMSO-d$_6$, δ, ppm, characteristic signals): 0.63 (d, 3H, J=7 Hz, CH$_3$-16); 0.81 (d, 3H, J=7 Hz, CH$_3$-17); 1.03 (s, 3H, CH$_3$-18); 1.34 (s, 3H, CH$_3$-15); 2.39

(bs, 1H, H-4); ABX-system ($u_A$=2.97, $u_B$=2.89, $J_{AB}$=14 Hz, $J_{AX}$=7 Hz, $J_{BX}$=7 Hz, CH$_2$-29); 3.39 (t, 1H, J=6 Hz, H-11); 3.92 (t, 1H, J=7 Hz, H-28); ABX-system ($u_A$=4.25, $u_B$=4.19, $J_{AB}$=15 Hz, $J_{AX}$=6 Hz, $J_{BX}$=6 Hz, CH$_2$-27); AB-system ($u_A$=4.70, $u_B$=4.62, J=17 Hz, CH$_2$-22); 5.01 and 5.07 (2×dd, 2H, J=2 and 11 Hz; J=2 and 18 Hz, H-20); 5.60 (d, 1H, J=8 Hz, H-14); 6.11 (dd, 1H, J=11 and 18 Hz, H-19); 6.65 (d, 2H, J=8 Hz, H-24); 6.68 (d, 2H, J=8 Hz, H-31); 6.76 (dd, 1H, J=2 and 8 Hz, H-26); 6.79 (bs, 1H, H-23); 7.00 (d, 2H, J=8 Hz, H-30); 7.17 (t, 1H, J=8 Hz, H-25).

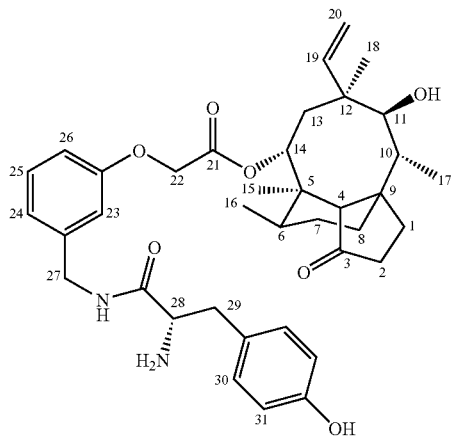

Example 35

14-O-[(3-{[(R)-2-Amino-3-(4-hydroxy-phenyl)-propionylamino]-methyl}-phenoxy)-acetyl]-mutilin hydrochloride $^1$H-NMR (400 MHz, DMSO-d$_6$, δ, ppm, characteristic signals): 0.63 (d, 3H, J=7 Hz, CH$_3$-16); 0.80 (d, 3H, J=7 Hz, CH$_3$-17); 1.02 (s, 3H, CH$_3$-18); 1.34 (s, 3H, CH$_3$-15); 2.40 (bs, 1H, H-4); ABX-system ($u_A$=2.96, $u_B$=2.88, $J_{AB}$=14 Hz, $J_{AX}$=7 Hz, $J_{BX}$=7 Hz, CH$_2$-29); 3.41 (t, 1H, J=6 Hz, H-11); 3.92 (t, 1H, J=7 Hz, H-28); 4.23 (m, 2H, CH$_2$-27); AB-system ($u_A$=4.71, $u_B$=4.62, J=17 Hz, CH$_2$-22); 5.01 and 5.07 (2×dd, 2H, J=2 and 11 Hz; J=2 and 18 Hz, H-20); 5.60 (d, 1H, J=8 Hz, H-14); 6.11 (dd, 1H, J=11 and 18 Hz, H-19); 6.65 (d, 2H, J=8 Hz, H-24); 6.68 (d, 2H, J=8 Hz, H-31); 6.76 (dd, 1H, J=2 and 8 Hz, H-26); 6.79 (bs, 1H, H-23); 6.99 (d, 2H, J=8 Hz, H-30); 7.17 (t, 1H, J=8 Hz, H-25).

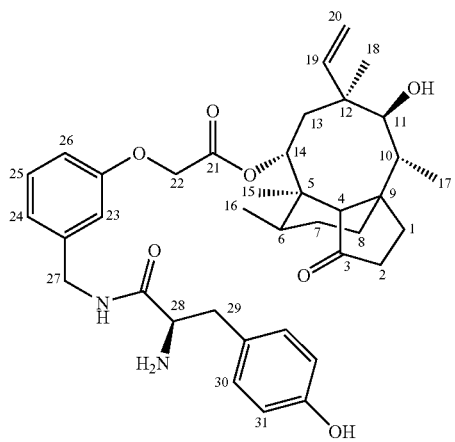

Example 36

14-O-[(3-{[((R)-Pyrrolidine-2-carbonyl)-amino]-methyl}-phenoxy)-acetyl]-19,20-dihydromutilin hydrochloride Step 1: 14-O-[(3-Aminomethyl-phenoxy)-acetyl]-19,20-dihydromutilin 5.3 g (10.4 mmol) of 14-O-[(3-Azidomethyl-phenoxy)-acetyl]-mutilin is dissolved in 160 mL of THF, 4.8 g of Lindlar-catalyst is added and the reaction mixture hydrogenated for 65 h at ambient temperature. The reaction mixture is filtered through celite, concentrated under reduced pressure and the residue is chromatographed on silica using CH$_2$Cl$_2$/MeOH 10:1 as mobile phase.

$^1$H-NMR (400 MHz, DMSO-d$_6$, δ, ppm, characteristic signals): 0.61 (t, 3H, J=7 Hz, CH$_3$-20); 0.64 (d, 3H, J=7 Hz, CH$_3$-16); 0.80 (d, 3H, J=7 Hz, CH$_3$-17); 0.84 (s, 3H, CH$_3$-18), 1.33 (s, 3H, CH$_3$-15); 2.36 (bs, 1H, H-4); 3.34 (t, 1H, J=6 Hz, H-11); 3.64 (s, 2H, CH$_2$-27); AB-system ($u_A$=4.71, $u_B$=4.62, J=17 Hz, CH$_2$-22); 5.58 (d, 1H, J=8 Hz, H-14); 6.70 (dd, 1H, J=2 and 8 Hz; H-26); 6.87 (bs, 1H, H-23); 6.90 (d, 1H, J=8 Hz, H-24); 7.16 (t, 1H, J=8 Hz, H-25).

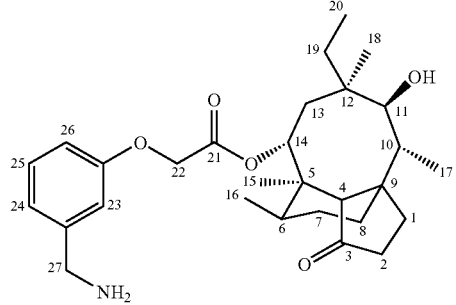

Step 2: 14-O-[(3-{[((R)-tert-Butoxycarbonylpyrrolidine-2-carbonyl)-amino]-methyl}-phenoxy)-acetyl]-19,20-dihydromutilin To 300 mg (0.62 mmol) of 14-O-[(3-Aminomethyl-phenoxy)-acetyl]-mutilin in 6 mL of THF is added 212 mg (0.99 mmol) of BOC-D-Praline together with 204 mg (0.99 mmol) of DCC and 75 mg (0.62 mmol) of DMAP. The reaction is stirred for 12 h at ambient temperature, the formed precipitate is filtered off and the filtrate is evaporated to dryness under reduced pressure. The residue is chromatographed on silica using dichloromethane/methanol 100:2 as mobile phase.

$^1$H-NMR (400 MHz, DMSO-d$_6$, δ, ppm, characteristic signals): 0.61 (t, 3H, J=7 Hz, CH$_3$-20); 0.64 (d, 3H, J=7 Hz, CH$_3$-16); 0.80 (d, 3H, J=7 Hz, CH$_3$-17); 0.84 (s, 3H, CH$_3$-18), 1.27 (bs, 9H, CH$_3$-32); 1.39 (s, 3H, CH$_3$-15); 2.36 (bs, 1H, H-4); 3.35 (2×m, 3H, CH$_2$-31 and H-11); 4.10 and 4.26 (2×m, 3H, CH$_2$-27 and H-28); AB-system ($u_A$=4.70, $u_B$=4.60, J=17 Hz, CH$_2$-22); 5.58 (d, 1H, J=8 Hz, H-14); 6.72 (m, 1H, H-26); 6.80 (bs, 1H, H-23); 6.72 (bd, 1H, J=8 Hz, H-24); 7.17 (m, 1H, H-25).

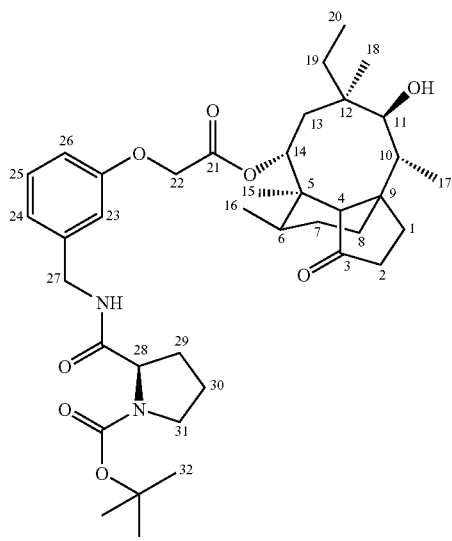

Step 3: 14-O-[(3-{[((R)-Pyrrolidine-2-carbonyl)-amino]-methyl}-phenoxy)-acetyl]-19,20-dihydromutilin hydrochloride 337 mg of 14-O-[(3-{[((R)-BOC-Piperidine-2-carbonyl)-amino]-methyl}-phenylsulfanyl)-acetyl]-mutilin is dissolved in 2 mL of dichloromethane and 5 mL of HCl-saturated Et$_2$O was added. The reaction was left at ambient temperature for 4 h and evaporated to dryness under reduced pressure.

$^1$H-NMR (400 MHz, DMSO-d$_6$, δ, ppm, characteristic signals): 0.61 (t, 3H, J=7 Hz, CH$_3$-20); 0.63 (d, 3H, J=7 Hz, CH$_3$-16); 0.79 (d, 3H, J=7 Hz, CH$_3$-17); 0.84 (s, 3H, CH$_3$-18), 1.33 (s, 3H, CH$_3$-15); 2.36 (bs, 1H, H-4); 3.18 (m, 2H, CH$_2$-31); 3.32 (t, 1H, J=6 Hz, H-11); 4.18 (t, 1H, J=7 Hz, H-28); 4.29 (d, 2H, J=6 Hz, CH$_2$-27); AB-system (u$_A$=4.74, u$_B$=4.63, J=17 Hz, CH$_2$-22); 5.58 (d, 1H, J=8 Hz, H-14); 6.78 (dd, 1H, J=2 and 8 Hz; H-26); 6.83 (d, 1H, J=2 Hz, H-23); 6.85 (d, 1H, J=8 Hz, H-24); 7.22 (t, 1H, J=8 Hz, H-25).

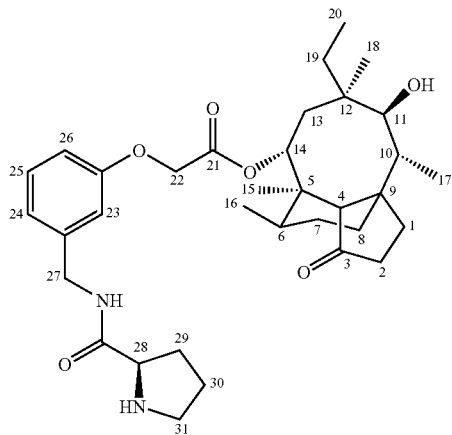

The following compounds are prepared in a similar fashion:

Example 37

14-O-[(3-{[((R)-2-Amino-3-hydroxy)-propionylamino]-methyl}-phenoxy)-acetyl]-19,20-dihydromutilin hydrochloride $^1$H-NMR (400 MHz, DMSO-d$_6$, δ, ppm, characteristic signals): 0.61 (t, 3H, J=7 Hz, CH$_3$-20); 0.63 (d, 3H, J=7 Hz, CH$_3$-16); 0.79 (d, 3H, J=7 Hz, CH$_3$-17); 0.84 (s, 3H, CH$_3$-18); 1.34 (s, 3H, CH$_3$-15); 2.36 (bs, 1H, H-4); 3.38 (t, 1H, J=6 Hz, H-11); 3.77 (m, 2H, CH$_2$-29); 3.86 (m, 1H, H-28); 4.29 (t, 2H, J=6 Hz, CH$_2$-27); AB-system (u$_A$=4.73, u$_B$=4.62, J=17 Hz, CH$_2$-22); 5.59 (d, 1H, J=8 Hz, H-14); 6.77 (dd, 1H, J=2 and 8 Hz, H-26); 6.84 (bs, 1H, H-23); 6.87 (d, 1H, J=8 Hz, H-24); 7.20 (t, 1H, J=8 Hz, H-25).

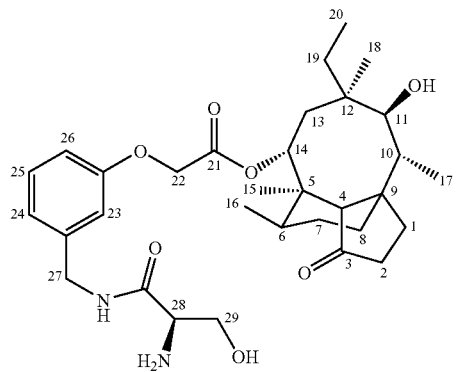

Example 38

14-O-[(3-{[(S)-2-Amino-3-(4-hydroxy-phenyl)-propionylamino]-methyl}-phenoxy)-acetyl]-19,20-dihydromutilin hydrochloride $^1$H-NMR (400 MHz, DMSO-d$_6$, δ, ppm, characteristic signals): 0.61 (t, 3H, J=7 Hz, CH$_3$-20); 0.64 (d, 3H, J=7 Hz, CH$_3$-16); 0.79 (d, 3H, J=7 Hz, CH$_3$-17); 0.84 (s, 3H, CH$_3$-18); 1.33 (s, 3H, CH$_3$-15); 2.36 (bs, 1H, H-4); ABX-system (u$_A$=2.96, u$_B$=2.88, J$_{AB}$=15 Hz, J$_{AX}$=7 Hz, J$_{BX}$=7 Hz, CH$_2$-29); 3.34 (t, 1H, J=6 Hz, H-11); 3.92 (t, 1H, J=7 Hz, H-28); 4.22 (m, 2H, CH$_2$-27); AB-system (u$_A$=4.72, u$_B$=4.62, J=17 Hz, CH$_2$-22); 5.58 (d, 1H, J=8 Hz, H-14); 6.65 (d, 1H, J=8 Hz, H-24); 6.68 (d, 2H, J=8 Hz, H-31); 6.77 (dd, 1H, J=2 and 8 Hz, H-26); 6.80 (bs, 1H, H-23); 7.00 (d, 2H, J=8 Hz, H-30); 7.16 (t, 1H, J=8 Hz, H-25).

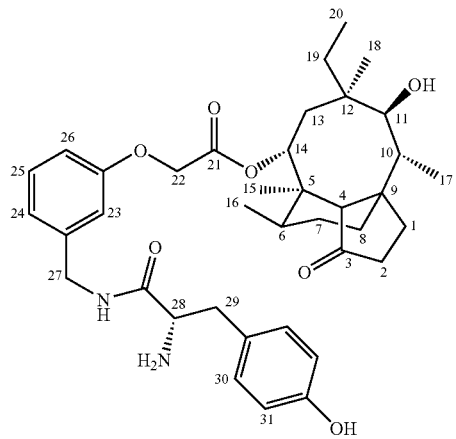

Example 39 (Comparison)

14-O-[(3-Methyl-phenylsulfanyl)-acetyl]-mutilin

Example 39 was prepared in analogy to Example 1, step 2.
¹H-NMR (400 MHz, DMSO-d₆, δ, ppm, characteristic signals): 0.56 (d, 3H, J=7 Hz, CH₃-16); 0.79 (d, 3H, J=7 Hz, CH₃-17); 0.97 (s, 3H, CH₃-18); 1.30 (s, 3H, CH₃-15); 2.24 (s, 3H, CH₃-27); 2.35 (bs, 1H, H-4); 3.37 (t, 1H, J=6 Hz, H-11); AB-system (u$_A$=3.80, u$_B$=3.73, J=16 Hz, CH₂-22); 4.94 (m, 2H, H-20); 5.48 (d, 1H, J=8 Hz, H-14); 6.03 (dd, 1H, J=11, and 18 Hz, H-19); 6.98 and 7.23 (2×m, 4H, arom-H).

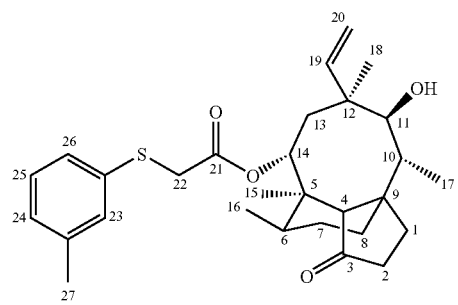

Example 40 (Comparison)

14-O-[(3-Methyl-phenoxy)-acetyl]-mutilin

Example 40 was prepared in analogy to Example 32, step 1.
¹H-NMR (400 MHz, DMSO-d₆, δ, ppm, characteristic signals): 0.64 (d, 3H, J=7 Hz, CH₃-16); 0.81 (d, 3H, J=7 Hz, CH₃-17); 1.04 (s, 3H, CH₃-18); 1.33 (s, 3H, CH₃-15); 2.23 (s, 3H, CH₃-27); 2.40 (bs, 1H, H-4); 3.41 (bs, 1H, H-11); AB-system (u$_A$=4.68, u$_B$=4.62, J=17 Hz, CH₂-22); 5.01 and 5.06 (2×d, 2H, J=11 Hz and 18 Hz, H-20); 5.60 (d, 1H, J=8 Hz, H-14); 6.11 (dd, 1H, J=11, and 18 Hz, H-19); 6.67 and 6.77 (2×d, 2H, J=7 Hz, H-24 and 26); 6.68 (s, 1H, H-23); 7.12 (t, 1H, J=8 Hz, H-25).

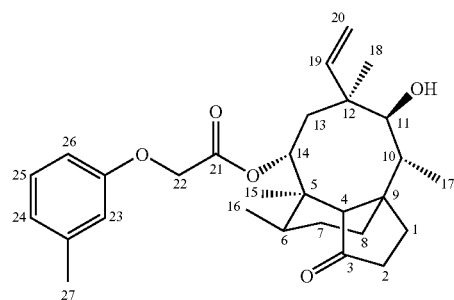

Example 41 (Comparison)

14-O-[(3-Methyl-phenoxy)-acetyl]-19,20-dihydro-mutilin

Example 41 was prepared by hydrogenation of the product of example 40 with Pd/C.

¹H-NMR (400 MHz, DMSO-d₆, δ, ppm, characteristic signals): 0.64 (d, 3H, J=7 Hz, CH₃-16); 0.81 (d, 3H, J=7 Hz, CH₃-17); 1.04 (s, 3H, CH₃-18); 1.33 (s, 3H, CH₃-15); 2.23 (s, 3H, CH₃-27); 2.40 (bs, 1H, H-4); 3.41 (bs, 1H, H-11); AB-system (u$_A$=4.68, u$_B$=4.62, J=17 Hz, CH₂-22); 5.01 and 5.06 (2×d, 2H, J=11 Hz and 18 Hz, H-20); 5.60 (d, 1H, J=8 Hz, H-14); 6.11 (dd, 1H, J=11, and 18 Hz, H-19); 6.67 and 6.77 (2×d, 2H, J=7 Hz, H-24 and 26); 6.68 (s, 1H, H-23); 7.12 (t, 1H, J=8 Hz, H-25).

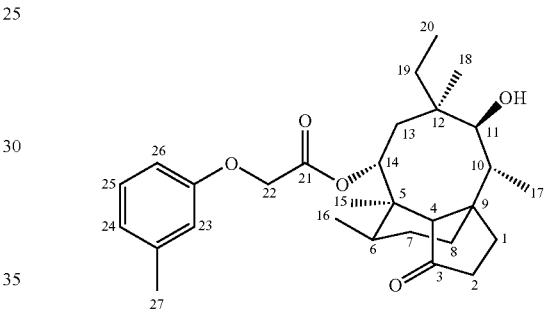

Antimicrobial Activity of Novel Pleuromutilin-derivatives with Aromatic Side-chain The antibacterial activity expressed as minimal inhibitory concentration (MIC) was determined according to the approved standard reference recommendations of CLSI (former NCCLS).

Example 1 and the other claimed compounds exhibited very good activity against the clinical relevant bacterial pathogens *Staphylococcus aureus, Enterococcus faecalis, Streptococcus pneumoniae, Moraxella catarrhalis* and *Escherichia coli* (see Table 1). This in vitro activity was significantly better than that of the comparator compounds examples 39-41, as the MICs of example 1 were by at least a factor of 2 lower against at least one of the strains shown in Table 1 than the MICs of examples 39-41 (see Table 1).

TABLE 1

Antimicrobial activity of example 1 and the comparator compounds examples 39-41 against selected bacterial pathogens shown as minimal inhibitory concentration (MIC, [μg/ml]).

| Species | ATCC number | Strain | Example 1* (3-mercaptobenzyl-piperidine-2-carboxamide mutilin deriv.) | Example 39* (3-mercapto-toluene) | Example 40* (3-hydroxy-toluene) | Example 41** (3-hydroxy-toluene) |
|---|---|---|---|---|---|---|
| Staphylococcus aureus (MSSA) | ATCC10390 | B6 | ≦0.0125 | 0.025 | 0.05 | 0.05 |
| Staphylococcus aureus (MSSA) | ATCC29213 | B7 | ≦0.0125 | 0.05 | 0.05 | 0.1 |
| Enterococcus faecalis | ATCC29212 | B4 | 1.6 | >6.4 | >6.4 | >6.4 |
| Enterococcus faecalis | ATCC51299 | B5 | 1.6 | >6.4 | >6.4 | >6.4 |
| Moraxella catarrhalis | ATCC43618 | B407 | 0.0125 | 0.0125 | 0.0125 | 0.025 |
| Escherichia coli | ATCC25922 | B1 | 12.8 | >6.4 | >6.4 | >6.4 |
| Streptococcus pneumoniae | ATCC49619 | B11 | ≦0.0025 | 0.16 | 0.64 | >0.64 |

*Pleuromutilin derivatives
**19,20-Dihydropleuromutilin derivative

The invention claimed is:

1. A compound of formula (I) or formula (II);

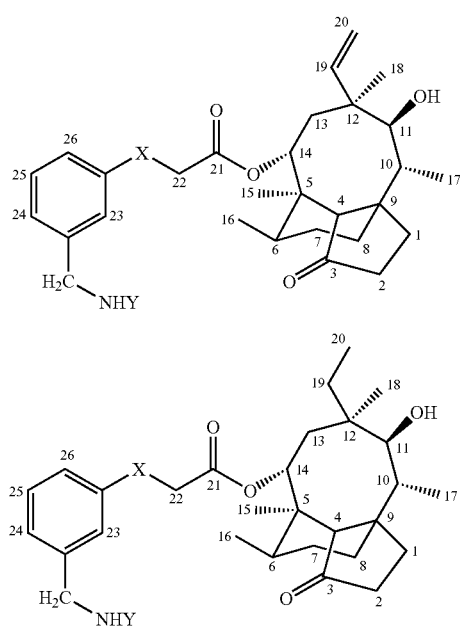

wherein
X is oxygen or sulfur, and
Y is a residue of pipecolic acid or a residue of an amino acid.

2. A compound selected from the group consisting of:
14-O-[(3-{[((R)-Piperidine-2-carbonyl)-amino]-methyl}-phenylsulfanyl)-acetyl]-mutilin,
14-O-[(3-{[((R)-2-Amino-3-methyl)-butyroylamino]-methyl}-phenylsulfanyl)-acetyl]-mutilin,
14-O-[(3-{[((2R,4R)-4-Hydroxy-pyrrolidine-2-carbonyl)-amino]-methyl}-phenylsulfanyl)-acetyl]-mutilin,
14-O-[(3-{[(S)-2-Amino-3-(3H-imidazol-4-yl)-propionylamino]-methyl}-phenylsulfanyl)-acetyl]-mutilin,
14-O-[(3-{[(R)-2-Amino-propionylamino]-methyl}-phenylsulfanyl)-acetyl]-mutilin,
14-O-[(3-{[2-(2-Amino-acetylamino)-acetylamino]-methyl}-phenylsulfanyl)-acetyl]-mutilin,
14-O-[(3-{[((R)-Pyrrolidine-2-carbonyl)-amino]-methyl}-phenylsulfanyl)-acetyl]-mutilin,
14-O-[(3-{[(R)-2-Amino-3-(4-hydroxy-phenyl)-propionylamino]-methyl}-phenylsulfanyl)-acetyl]-mutilin,
14-O-[(3-{[2-Amino-acetylamino]-methyl}-phenylsulfanyl)-acetyl]-mutilin,
14-O-[(3-{[(S)-2-((S)-2-Amino-propionylamino)-propionylamino]-methyl}-phenylsulfanyl)-acetyl]-mutilin,
14-O-[(3-{[((S)-2-Amino-3-methyl)-butyroylamino]-methyl}-phenylsulfanyl)-acetyl]-mutilin,
14-O-[(3-{(2-[((R)-Pyrrolidine-2-carbonyl)-amino]-acetylamino)-methyl}-phenylsulfanyl)-acetyl]-mutilin,
14-O-[(3-{[((2R,3S)-2-Amino-3-hydroxy)-butyroylamino]-methyl}-phenylsulfanyl)-acetyl]-mutilin,
14-O-[(3-{[(R)-2,6-Diamino-hexanoylamino]-methyl}-phenylsulfanyl)-acetyl]-mutilin,
14-O-[(3-{[(R)-2-Amino-3-(1H-indol-3-yl)-propylamino]-methyl}-phenylsulfanyl)-acetyl]-mutilin,
14-O-[(3-{[(R)-2-Amino-3-phenyl-propionylamino]-methyl}-phenylsulfanyl)-acetyl]-mutilin,
14-O-[(3-{[(R)-2-Amino-3-carbamoyl-propionylamino]-methyl}-phenylsulfanyl)-acetyl]-mutilin,
14-O-[(3-{[(S)-2,6-Diamino-hexanoylamino]-methyl}-phenylsulfanyl)-acetyl]-mutilin,
14-O-[(3-{[(S)-2((S)-2-Amino-4-methyl-pentanoylamino)-4-methyl-pentanoylamino]-methyl}-phenylsulfanyl)-acetyl]-mutilin,
14-O-[(3-{[((R)-2-Amino-3-hydroxy)-propionylamino]-methyl}-phenylsulfanyl)-acetyl]-mutilin, 14-O-[(3-{[(S)-2-Amino-propylamino]-methyl}-phenylsulfanyl)-acetyl]-mutilin, 14-O-[(3-{[(R)-2-Amino-4-carbamoyl-butyroylamino]-methyl}-phenylsulfanyl)-acetyl]-mutilin, 14-O-[(3-{[((S)-1-(2-Amino-acetyl)-pyrrolidine-2-carbonyl)-amino]-methyl}-phenylsulfanyl)-acetyl]-mutilin, 14-O-[(3-{[(R)-2-Amino-3-(3H-imidazol-4-yl)-propionylamino]-methyl}-phenylsulfanyl)-acetyl]-mutilin, 14-O-[(3-{[((2S,4R)-4-Hydroxy-pyrrolidine-2-carbonyl)-amino]-methyl}-phenylsulfanyl)-acetyl]-mutilin, 14-O-[(3-{[((S)-Piperidine-2-carbonyl)-amino]-methyl}-phenylsulfanyl)-acetyl]-mutilin, 14-O-[(3-{[((S)-Pyrrolidine-2-carbonyl)-amino]-methyl}-phenylsulfanyl)-acetyl]-mutilin, 14-O-[(3-{[(S)-2-Amino-3-(4-hydroxy-phenyl)-propionylamino]-methyl}-phenylsulfanyl)-acetyl]-mutilin, 14-O-[(3-{[(S)-2-Amino-3-phenyl-propionylamino]-methyl}-phenylsulfanyl)-acetyl]-mutilin, 14-O-[(3-{[((S)-2-Amino-3-hydroxy)-propionylamino]-methyl}-phenylsulfanyl)-acetyl]-mutilin, 14-O-[(3-{[((2S,3R)-2-Amino-3-hydroxy)-butyroylamino]-methyl}-phenylsulfanyl)-acetyl]-mutilin, 14-O-[(3-{[((R)-2-Amino-3-hydroxy)-propionylamino]-methyl}-phenoxy)-acetyl]-mutilin, 14-O-[(3-{[((R)-Pyrrolidine-2-carbonyl)-amino]-methyl}-phenoxy)-acetyl]-mutilin, 14-O-[(3-{[(S)-2-Amino-3-(4-hydroxy-phenyl)-propionylamino]-methyl}-phenoxy)-acetyl]-mutilin, 14-O-[(3-{[(R)-2-Amino-3-(4-hydroxy-phenyl)-propionylamino]-methyl}-phenoxy)-acetyl]-mutilin, 14-O-[(3-{[((R)-Pyrrolidine-2-carbonyl)-amino]-methyl}-phenoxy)-acetyl]-19,20-dihydromutilin, 14-O-[(3-{[((R)-2-Amino-3-hydroxy)-propionylamino]-methyl}-phenoxy)-acetyl]-19,20-dihydromutilin, or 14-O-[(3-{[(S)-2-Amino-3-(4-hydroxy-phenyl)-propionylamino]-methyl}-phenoxy)-acetyl]-19,20-dihydromutilin.

3. The compound of claim 1, in the form of a salt.

4. The compound of claim 1, wherein the compound is in a pharmaceutical composition.

5. A method of treatment of bacterial diseases, which comprises:
   administering to a subject in need of such treatment an effective amount of a compound of claims 1.

6. A method of manufacturing a composition for treatment of bacterial diseases, the method comprising:
   obtaining a compound according to claim 1; and
   including the compound in a medicament for the treatment of bacterial diseases.

7. The method of claim 5, wherein the bacterial disease is a skin or soft tissue infection.

8. A pharmaceutical composition comprising:
   a compound of claim 1 in association with at least one pharmaceutical excipient.

9. The pharmaceutical composition of claim 8, further comprising another pharmaceutically active agent.

10. The compound of claim 2, in the form of a salt.

11. A method of treatment of bacterial diseases, which method comprises:
    administering to a subject in need of such treatment an effective amount of a compound of claim 2.

12. The method of claim 11, wherein the bacterial diseases is a skin or soft tissue infection.

13. A method of treatment of bacterial diseases, which method comprises:
    administering to a subject in need of such treatment an effective amount of a compound of claim 3.

14. The method of claim 13, wherein the bacterial diseases is a skin or soft tissue infection.

15. A method of treatment of bacterial diseases, which method comprises:
    administering to a subject in need of such treatment an effective amount of a compound of claim 4.

16. The method of claim 15, wherein the bacterial diseases is a skin or soft tissue infection.

17. A pharmaceutical composition comprising:
    a compound of claim 2 in association with at least one pharmaceutical excipient.

18. A pharmaceutical composition comprising:
    a compound of claim 3 in association with at least one pharmaceutical excipient.

19. A pharmaceutical composition comprising:
    a compound of claim 4 in association with at least one pharmaceutical excipient.

* * * * *

UNITED STATES PATENT AND TRADEMARK OFFICE
CERTIFICATE OF CORRECTION

PATENT NO. : 8,173,685 B2  
APPLICATION NO. : 12/668769  
DATED : May 8, 2012  
INVENTOR(S) : Thirring et al.

Page 1 of 1

It is certified that error appears in the above-identified patent and that said Letters Patent is hereby corrected as shown below:

In the Specifications:

Column 3
Line 16, change "clinical" to --clinically--
Line 56, change "include for example" to --include, for example,--

Column 5
Line 31, change "*Helicobacter*" to --*Helicobacter*,--

Column 6
Line 19, change "pharmaceutically" to --pharmaceutical--

Column 8
Line 58-59, change "The organic phase is dried with anhydrous sodium sulfate and concentrated under reduced pressure. The organic" to --The organic--

Column 10
Line 30, change "ar" to --at--

In the Claims:

Column 40
Claim 12, Line 22, change "is a skin or soft tissue infection." to --are skin or soft tissue infections.--
Claim 14, Line 28, change "is a skin or soft tissue infection." to --are skin or soft tissue infections.--
Claim 16, Line 33, change "is a skin or soft tissue infection." to --are skin or soft tissue infections.--

Signed and Sealed this
Sixteenth Day of July, 2013

Teresa Stanek Rea
*Acting Director of the United States Patent and Trademark Office*